(12) United States Patent
Prasad et al.

(10) Patent No.: US 9,500,624 B2
(45) Date of Patent: Nov. 22, 2016

(54) SYSTEM COMPRISING A MASS SPECTROMETER COUPLED TO A FAIMS APPARATUS AND METHODS OF OPERATION

(71) Applicant: Thermo Finnigan LLC, San Jose, CA (US)

(72) Inventors: Satendra Prasad, San Jose, CA (US); Jean-Jacques Dunyach, San Jose, CA (US); Michael Belford, Los Altos, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 14/738,089

(22) Filed: Jun. 12, 2015

(65) Prior Publication Data

US 2015/0362461 A1    Dec. 17, 2015

Related U.S. Application Data

(60) Provisional application No. 62/012,063, filed on Jun. 13, 2014.

(51) Int. Cl.
*G01N 27/62* (2006.01)
*H01J 49/00* (2006.01)
*G01N 30/72* (2006.01)

(52) U.S. Cl.
CPC ........ *G01N 27/624* (2013.01); *G01N 30/7233* (2013.01); *H01J 49/004* (2013.01); *H01J 49/0031* (2013.01)

(58) Field of Classification Search
CPC .................... H01J 49/0031; G01N 27/624
See application file for complete search history.

(56) References Cited

U.S. PATENT DOCUMENTS 6,713,758 B2    3/2004  Guevremont et al.
7,034,286 B2    4/2006  Guevremont et al.
(Continued)

FOREIGN PATENT DOCUMENTS

WO    WO 01/69216 A2       9/2001
WO    WO 2012/167254 A1    12/2012
WO    WO 2013/140132 A2    9/2013

OTHER PUBLICATIONS

Creese, et al., "Probing the Complementarity of FAIMS and Strong Cation Exchange Chromatography in Shotgun Proteomics", J. Am. Soc. Mass Spectrom. 2013, (24), pp. 431-443.
(Continued)

*Primary Examiner* — Wyatt Stoffa
*Assistant Examiner* — Eliza Osenbaugh-Stewar
(74) *Attorney, Agent, or Firm* — Thomas F. Cooney

(57) ABSTRACT

A method of operating a system comprising a chromatograph and a mass spectrometer comprises: (a) providing an abundance threshold and a list comprising respective entries for precursor ion species of interest comprising respective precursor-ion m/z ratios; (b) transmitting a first sample fraction portion comprising a plurality of sample-fraction ion species through an ion mobility spectrometer operated in non-dispersive mode to the mass spectrometer; (c) detecting a respective abundance at each of a plurality of sample-fraction m/z ratios; and (d) upon detection of an above-threshold ion abundance at an m/z-ratio corresponding to a first precursor ion species of interest: (d1) inletting a second sample fraction portion into the ion mobility spectrometer operated in dispersive mode such that ions of the first precursor-ion species are preferentially transmitted therethrough; (d2) fragmenting the preferentially-transmitted ions so as to generate product ion species; and (d3) detecting the product ion species.

14 Claims, 17 Drawing Sheets

(56) References Cited

U.S. PATENT DOCUMENTS

| | | |
|---|---|---|
| 7,034,289 B2 | 4/2006 | Guevremont et al. |
| 7,223,967 B2 | 5/2007 | Guevremont et al. |
| 7,468,511 B2 | 12/2008 | Belford |
| 2002/0134932 A1 | 9/2002 | Guevremont et al. |
| 2006/0237643 A1 | 10/2006 | Guevremont et al. |
| 2009/0159796 A1 | 6/2009 | Belford et al. |
| 2010/0264306 A1 | 10/2010 | Rorrer, III et al. |
| 2011/0253890 A1 | 10/2011 | Belford et al. |
| 2012/0018631 A1* | 1/2012 | Giles .................... G01N 27/624 250/282 |
| 2013/0306860 A1 | 11/2013 | Prasad et al. |
| 2015/0028196 A1 | 1/2015 | Toutoungi et al. |
| 2015/0041636 A1* | 2/2015 | Giles .................... H01J 49/004 250/282 |

OTHER PUBLICATIONS

Valentine, et al., "Developing liquid chromatography ion mobility mass spectrometry techniques", Expert Rev. Proteomics 2005, 2 (4), pp. 553-565.

* cited by examiner

SYSTEM COMPRISING A MASS SPECTROMETER COUPLED TO A FAIMS APPARATUS AND METHODS OF OPERATION

CROSS REFERENCE TO RELATED APPLICATION

This application claims priority to and the benefit of the filing date, under 35 U.S.C. 119(e), of U.S. Provisional Application for Patent No. 62/012,063, filed on Jun. 13, 2014 and titled "System Comprising a Mass Spectrometer coupled to a FAIMS Apparatus and Methods of Operation", said Provisional application assigned to the assignee of the present invention and incorporated herein by reference.

FIELD OF THE INVENTION

The present invention relates generally to the field of mass spectrometry and, more particularly, relates to a system comprising a mass spectrometer apparatus that is coupled to and receives ions from an ion-mobility spectrometer, such as a high-field asymmetric ion mobility spectrometer (FAIMS) apparatus.

BACKGROUND OF THE INVENTION

Liquid chromatography-mass spectrometry (LC/MS) is an extremely useful technique for detection, identification and (or) quantification of components of mixtures or of analytes within mixtures. As is known, liquid chromatography is a fractionation separation process. Accordingly, a liquid chromatograph instrument generally operates so as to separate a sample that is a complex mixture of substances into separate fractions. The individual fractions have simpler compositions than the original sample and the composition of each fraction can (but may not) approach that of a purified substance. The fraction compositions systematically vary from one another according to a gradient. The LC/MS technique generally provides data in the form of a mass chromatogram, in which detected ion intensity (a measure of the number of detected ions) as measured by a mass spectrometer is given as a function of time. In the LC/MS technique, various separated chemical constituents elute from a chromatographic column as a function of time. As these constituents elute off the column, they are submitted for mass analysis by a mass spectrometer at which each analyte or chromatographic fraction is ionized, generally producing a variety of ions from each such analyte or fraction. The mass spectrometer accordingly generates, in real time, detected relative ion abundance data for ions produced from each eluting analyte or each chromatographic fraction, in turn.

The term "liquid chromatography" includes, without limitation, reverse phase liquid chromatography (RPLC), hydrophilic interaction liquid chromatography (HILIC), high performance liquid chromatography (HPLC), ultra high performance liquid chromatography (UHPLC), normal-phase high performance liquid chromatography (NP-HPLC), supercritical fluid chromatography (SFC) and ion chromatography.

One can often enhance the specificity of the mass spectrometry technique by employing "tandem mass spectrometry" or "MS/MS", for example via use of a triple quadrupole mass spectrometer. In the MS/MS technique, a parent (or precursor) ion generated from a molecule of interest can be filtered or isolated in an MS instrument (for instance, in a quadrupole mass filter, Q1, of a triple quadrupole instrument), and these precursor ions are subsequently fragmented (e.g., in a second quadrupole, Q2) to yield multiple product or fragment ions that are then analyzed in a downstream MS stage (e.g., in a third quadrupole, Q3). By careful selection of precursor ion and product ion species, the presence and/or concentrations of various analytes of interest can be determined with specificity. Multiple reaction monitoring (MRM) is performed by applying the above-described MS/MS procedure to multiple precursor/product ion pairs. When applied to the analysis of complex samples that are resolved using a liquid chromatograph (LC) to produce multiple constituents, the MRM technique provides sufficient throughput to screen or quantify a large fraction of the eluting analytes with high sensitivity and specificity.

An LC/MS analysis workflow that employs the MRM technique may be referred to as an LC-MRM analysis. During an LC-MRM analysis, the mass analyzer continuously cycles through all m/z ions included in a predetermined list for Q1 isolation over the duration of an LC gradient. The precursor m/z isolation (Q1 stage) only requires a few tens of milliseconds to isolate or filter ions comprising a single m/z range, thus permitting analysis of up to ~500 isolations per second. For example, consider the model case depicted in FIG. 8 in which a chromatographic peak having an approximately 12 second width at its base is mass analyzed by the MRM technique and the MRM precursor isolation list includes 100 m/z species to be targeted during an LC analysis. The 100 m/z isolations are represented by square blocks at the base of FIG. 8. Each of the vertical lines illustrated underneath the chromatographic peak profile 200 represents a single, representative first mass spectral MS/MS analysis out of 100 such analyses per cycle. The exemplary absolute time scale shown at the base of FIG. 8 as well as in FIGS. 10A and 10B, as well as the implied absolute time scales illustrated in FIGS. 11 and 12 should be understood as being referenced to an analysis start time which is taken as the origin of the time axis (i.e., is taken as "time zero" at which t=0. The analysis start may be chosen to correspond to some well-defined event, such as the opening of a valve that begins the flow of chromatographic mobile phase through a chromatographic column. A consistent definition of the starting event enables comparison of results across separate experiments.

The time increment between each pair of vertical lines in the top portion of FIG. 8 represents the cumulative time needed to step through all the 100 MS/MS analyses—each corresponding to a different respective m/z isolation—and is termed the cycle time. The process is iterative; thus, a new sweep through the full list is initiated at the time indicated by each vertical line. This iterative analytical process terminates at the end of an LC gradient. LC-MRM analysis is a popular technique for quantifying constituents—such as proteins and peptides in biological samples—whose abundances may vary by orders of magnitude. At low abundance, the quality of quantitation is dependent on ion statistics or by the % RSD of the integral of the analyte response. An analytically acceptable % RSD of <15% often requires at least 10 MS/MS analyses. For instance, assume that the Q1 dwell time required to perform a single MS/MS analysis is equal to 10 ms and that the inter-analysis delay is 2.0 ms. These instrumental parameters correspond to a cycle time of ~1.2 seconds per cycle, which is the time required to cycle through the 100 precursor/product ion pairs in the MRM list. Thus, during the elution of a ~12-second wide peak, which is typical for nano-flow rate chromatography, a total of 10 mass spectral analyses can be acquired for each such ion pair.

A key difference between a MRM analysis and other types of tandem LC/MS analyses is that, in a MRM analysis, the detection of a precursor ion m/z is not a criterion to initiate a MRM event. The mass analyzer continuously cycles through a predetermined list of precursor-product ion pairs over the duration of a LC gradient. Conversely, in data dependent tandem mass analysis, a precursor ion species of interest must be detected in a low collision energy pre-scan or MS survey scan. The survey scan reveals high-abundance precursor ions that are selected for dissociation and the product ions are analyzed in a MS/MS scan mode. Thus, the precursor ions are not predetermined (MRM) but, rather, detected during the survey scan.

Generally described, data-dependent acquisition, which is also referred to, in various commercial implementations, as Information Dependent Acquisition (IDA), Data Directed Analysis (DDA), intelligent SRM (iSRM) and AUTO MS/MS, involves using data derived from an experimentally-acquired mass spectrum in an "on-the-fly" or "real-time" manner to direct the subsequent operation of a mass spectrometer. Utilization of data-dependent acquisition methods in a mass spectrometer provides the ability to make automated, real-time decisions in order to maximize the useful information content of the acquired data, thereby avoiding or reducing the need to perform multiple chromatographic runs or injections of the analyte sample. These methods can be tailored for specific desired objectives, such as enhancing the number of peptide identifications from the analysis of a complex mixture of peptides derived from a biological sample.

Data-dependent acquisition methods may be characterized as having one or more input criteria, and one or more output actions. The input criteria employed for conventional data-dependent methods are generally based on parameters such as intensity, intensity pattern, mass window, mass difference (neutral loss), mass-to-charge (m/z) inclusion and exclusion lists, and product ion mass. The input criteria are employed to select one or more ion species that satisfy the criteria. The selected ion species are then subjected to an output action (examples of which include performing MS/MS or MS$^n$ analysis and/or high-resolution scanning). In one instance of a typical data-dependent experiment, a group of ions is mass analyzed, and ion species having mass spectral intensities exceeding a specified threshold are subsequently selected as precursor ions for MS/MS analysis, which may involve operations of isolation, dissociation of the precursor ions, and mass analysis of the product ions.

Many mass spectrometer systems employ an ion mobility apparatus between an ion source and the mass spectrometer apparatus in order to selectively filter the ions prior to mass spectrometric analysis. In ion mobility spectrometry devices, separation of gas-phase ions is accomplished by exploiting variations in ion drift velocities under an applied electric field arising from differences in ion mobility. One well-known type of ion mobility spectrometry device is the High Field Asymmetric Waveform Ion Mobility Spectrometry (FAIMS) cell, also known by the term Differential Ion Mobility Spectrometry (DMS) cell, which separates ions on the basis of a difference in the mobility of an ion at high field strength (commonly denoted as $K_h$) relative to the mobility of the ion at low field strength (commonly denoted as K).

U.S. Pat. No. 6,504,149, in the name of inventors Guevremont and Purves, teaches the coupling of a FAIMS apparatus to a mass spectrometer. Briefly described, a FAIMS cell comprises a pair of spaced apart electrodes that define therebetween a separation region through which a stream of ions is directed. An asymmetric oscillatory voltage waveform comprising a high voltage component and a lower voltage component of opposite polarity, together with a non-oscillatory DC voltage (referred to as the compensation voltage, or CV) is applied to one of the electrodes. When the ion stream contains several species of ions, generally only one ion species is selectively or preferentially transmitted through the FAIMS cell for a given combination of asymmetric waveform peak voltage (referred to as the dispersion voltage, or DV) and CV. The remaining species of ions drift toward one of the electrode surfaces and are neutralized. The FAIMS cell may be operated in single ion detection mode, wherein the DV and CV are maintained at constant values, or alternatively the applied CV may be scanned with time to sequentially transmit ion species having different mobilities. FAIMS cells may be used for a variety of purposes, including providing separation or filtering of an ion stream prior to entry into a mass analyzer. When used as a pre-filter for a mass spectrometer, the FAIMS apparatus provides a way of eliminating isobaric interference ions which might accidentally have a mass-to-charge ratio nearly identical to that of an analyte of interest.

FIG. 1 schematically depicts a first known system 100 for analyzing ions that includes a FAIMS device 155 coupled to a mass spectrometer 157. The known FAIMS device 155 illustrated in FIG. 1 is an example of a type of device that has been referred to as a "side-to-side FAIMS" or a "perpendicular-gas-flow-FAIMS" (e.g., see U.S. Pat. No. 6,713,758 and international application publication No. WO01/69216). A solution of sample to be analyzed is introduced as a spray of liquid droplets into an ionization chamber 105 via atmospheric pressure ion source 110. Ionization chamber 105 is maintained at a high pressure relative to the regions downstream in the ion path, typically at or near atmospheric pressure. Atmospheric pressure ion source 110 may be configured as an electrospray ionization (ESI) probe, wherein a high DC voltage (either positive or negative) is applied to the capillary or "needle" through which the sample solution flows. Other suitable ionization techniques may be utilized in place of ESI, including without limitation such well-known techniques as atmospheric pressure chemical ionization (APCI), heated electrospray ionization (HESI), and thermospray ionization.

Ions produced by the ion source enter the FAIMS cell 155 through an aperture 117 in an entrance plate 120 and then through an inlet orifice 150 after passing through an expansion chamber 111. The expansion chamber is provided with a gas, typically helium or other inert gas, which is introduced into the expansion chamber 111 via a gas conduit 113. A portion of the gas flows back into the ionization chamber 105 through entrance plate aperture 117 in counter-flow to the ions and droplets and serves to desolvate charged droplets. Another portion of the gas combines with the analyte ions in chamber 111 and serves as a carrier gas through the FAIMS cell 155. The combined ion/carrier gas flow then enters FAIMS cell 155 through inlet orifice 150. The carrier gas flow may be carefully metered to maintain flow rates within predetermined limits which will depend on the FAIMS cell size, electrode geometry, and operational considerations. An electrical potential difference is maintained between the entrance plate 120 and the FAIMS cell 155 and, thus, physical separation is maintained between these components. Accordingly, a non-conducting sealing element 173, such as a gasket or O-ring maintains the FAIMS gas within the apparatus and prevents contamination of this gas from outside air. Because of drawing-space limitations, this sealing element is not explicitly shown in some of the accompanying drawings.

Generally speaking, the side-to-side FAIMS cell 155 includes inner and outer electrodes 165 and 170 having radially opposed surfaces, which define therebetween an annular separation region 175 (an "analytical gap") through which the ions are transported. The side-to-side FAIMS cell geometry depicted in FIG. 1 as well as in other figures herein provides a configuration in which the longitudinal axes (axes of cylindrical surfaces, directed out of the page) of inner electrode 165 and outer electrode 170 are oriented transversely with respect to the overall direction of ion flow. The principles of the design and operation of FAIMS cells and other ion mobility spectrometry devices have been extensively described elsewhere in the art (see, for example, U.S. Pat. No. 6,639,212 to Guevremont et al., incorporated by reference herein in its entirety), and hence will not be described in detail herein. In brief, the carrier gas and ions flow through the separation region 175 from inlet orifice 150 to exit orifice 185. Ion separation is effected within the separation region (analytical gap) 175 of the FAIMS cell 155 by applying an asymmetric waveform having a peak voltage (DV) and a compensation voltage (CV) to one of the inner or outer electrodes, 165, 170. The values of CV and DV are set to allow transmission of a selected ion species through separation region 175. Other ion species having different relative values of high field and low field mobilities will migrate to the surface of one of the electrodes and will be neutralized.

Still referring to FIG. 1, the selected ions emerge from the FAIMS cell 155 through exit orifice 185 and pass through a small gap 183 separating the FAIMS cell 155 from a mass spectrometer 157. Whereas most of the carrier gas exhausts through the gap 183 at atmospheric pressure, ions are electrostatically guided into at least one reduced pressure chamber 188 of the mass spectrometer 157 through an orifice in the mass spectrometer or through an ion transfer tube 163. The at least one reduced pressure chamber may be evacuated by a vacuum port 191. At least a portion of ion transfer tube 163 may be surrounded by and in good thermal contact with a heat source, such as heater jacket 167. The heater jacket 167, which may take the form of a conventional resistance heater, is operable to raise the temperature of ion transfer tube 163 to promote further desolvation of droplets entering the ion transfer tube 163.

From the at least one reduced pressure chamber 188, ions are transferred through an orifice 193 of a skimmer 194 into a high vacuum chamber 195 maintained at a low pressure (typically around 100 millitorr) relative to the reduced pressure chamber 188. The high vacuum chamber 195 is typically evacuated by turbo or similar high-vacuum pumps via a vacuum port 197. The skimmer 194 may be fabricated from an electrically conductive material, and an offset voltage may be applied to skimmer 194 to assist in the transport of ions through interface region and into skimmer orifice 193. Ions passing through skimmer orifice 193 may be focused or guided through ion optical assembly 198, which may include various electrodes forming ion lenses, ion guides, ion gates, quadrupole or octopole rod sets, etc. The ion optical assembly 198 may serve to transport ions to an analyzer 199 for mass analysis. Analyzer 199 may be implemented as any one or a combination of conventional mass analyzers, including (without limitation) a quadrupole mass analyzer, ion trap, or time-of-flight analyzer.

The inlet orifice 150 of the conventional FAIMS apparatus 155 comprises a simple hole of circular cross section having a constant inner diameter. Recently, U.S. Pat. No. 8,664,593, which is assigned to the assignee of the instant invention, described side-to-side FAIMS apparatuses having curved ion inlet orifices which provide for more efficient transfer of analyte ions through the analytical gap. FIG. 2 shows the FAIMS gas flow into an electrode set that is provided with a so-modified ion inlet orifice. The modified ion inlet orifice acts to decrease the volume and rate of gas flow directly onto the inner electrode adjacent to the orifice, thus significantly reducing neutralization of analyte ions. Note that the inner electrode 165 is generally a right-circular cylindrical rod having an axis 177 that is parallel to the length of the rod (see FIG. 5A). In the cross sectional representations of FIG. 2 and FIG. 3, the axis 177 is perpendicular to the plane of the drawing and is thus indicated as a piercing point ("+" symbol).

The FAIMS apparatus 109 that is schematically illustrated in FIG. 2 is generally similar to the FAIMS apparatus 155 shown in FIG. 1 except with regard to the shape of the ion inlet orifice. Inset 30 of FIG. 2 illustrates an enlarged view of the vicinity of the ion inlet orifice 151 of the FAIMS 109. The walls 31 of the ion inlet orifice 151 of the FAIMS apparatus 109 are convexly curved between the orifice inlet end 32 and the orifice outlet end 33. Thus, the inner diameter of the ion inlet orifice is at a minimum value within the orifice. Because of the curvature, the inner diameter of the ion inlet orifice 151 smoothly increases or flares outward in both directions (i.e., towards the two ends of the orifice or, equivalently, towards and away from the inner electrode 177) away from the region of minimum diameter. The gas flow in the vicinity of the rounded walls of the ion inlet orifice 151, as determined by fluid dynamic calculations, demonstrates the so-called Coandă effect, which is the general tendency of a fluid jet to be drawn towards and follow the contour of a curved solid surface. By means of the Coandă effect, the carrier gas flow entering the analytical gap 175 of the FAIMS apparatus 109 (FIG. 2) is kept closer to the curvature of the entrance orifice than would otherwise be the case. This behavior allows for incorporation of the gas stream into the gap and away from the inner electrode as is indicated in FIG. 2 by the smooth divergence of gas flow vectors away from the center electrode 165 and into the analytical gap 175. The smooth divergence of the carrier gas into away from the center electrode and into the analytical gap 175 is expected to urge ions along similar pathways, thereby reducing the proportion of ions that are lost as a result of collision with the center electrode and improving ion transmission through the FAIMS apparatus. As indicated by the fluid dynamics calculations, the smooth divergence also leads to a larger zone of laminar flow within the analytical gap, with reduced recirculation flow near the entrance orifice.

FIG. 3 shows the results of combined fluid dynamic and ion trajectory modeling, through the FAIMS apparatus 109. FIG. 4 shows a comparison between the transmission efficiency (curve 42) of the apparatus having the curved an inlet orifice 151 and shown in FIG. 3 with that of the prior FAIMS apparatus shown in FIG. 1 (curve 44). It is evident from the shape of the ion cloud 129 in FIG. 3 that the curved orifice design promotes a smooth bifurcation of ion flow prior around the center electrode 165 and into the analytical gap 175. The smooth flow bifurcation appears to have the effect of reducing gas recirculation flow with the analytical gap just after passing through the inlet orifice, thereby significantly reducing ion neutralization at both inner and outer electrodes.

The simple re-design of the cross-sectional shape of the ion inlet orifice as described above improves the uniformity of flow of carrier gas through the FAIMS apparatus. This smoother flow is such that there is highly reduced flow rate of the carrier gas (and entrained ions) directly onto the electrodes, relative to the conventional FAIMS apparatus 155 (FIG. 1). This smoother flow is believed to have a major effect in yielding the results of FIG. 4, in which simulated CV scans through the FAIMS 109 and through the FAIMS 155 are shown as curves 42 and 44, respectively.

One of the limiting characteristics of conventional FAIMS apparatuses that have precluded them from being used on a mass spectrometer employing an LC/MS/MS workflow or other varieties of data-dependent acquisition has been the long transit time or residence time of ions through the FAIMS analyzer. The residence time required for ions to transit through the FAIMS analyzer gap can range between 50-100 ms. In general, there does not exist a simple one-to-one correspondence between differential ion mobility and ion m/z ratio. Thus, a mass analyzer that receives ions from a FAIMS apparatus should remain set to detect only the m/z value of a particular analyte ion species of interest during the entire time that the FAIMS is operated so as to transmit ions having the particular differential ion mobility associated with that particular analyte ion species. If the mass analyzer were to be set to detect a different m/z ratio during this time, generally no ions would be detected, since the FAIMS would generally eliminate all other ion species, based on their various values of differential ion mobility.

In accordance with the above considerations, the FAIMS residence time thus defines the period that the first mass analyzer (Q1) must spend on a single mass-to-charge ratio (m/z) isolation. As discussed above, Q1 only requires, at most, a few tens of milliseconds, in the absence of a FAIMS pre-filter, to isolate or filter ions comprising a single m/z range, thus permitting analysis of up to ~100 or more isolations per second. However, increasing the Q1 dwell time in order to match the 50-100 ms residence time of the conventional FAIMS apparatus may result in insufficient number of scans to define a stable chromatographic peak structure. This limitation is often reached when employing a FAIMS apparatus coupled to a mass spectrometer. Generally, the time between scans or the cycle time will be the dwell time plus the inter-scan-delay-time plus the ion residence time. Given the time requirements of the conventional FAIMS apparatus, the cycle time required to perform at least an MS scan for each one of the 100 precursors in the MRM list is approximately 10.2 seconds (as opposed to 1.2 seconds per cycle in the absence of the FAIMS). Thus, only one MS scan per precursor ion can be made across a 12-second wide LC peak.

Another limiting characteristic of conventional FAIMS that has precluded its large-scale use with an LC/MS/MS workflow or other data-dependent acquisition workflow has been the generally low ion throughput transmission of conventional FAIMS apparatuses (e.g., see curve 44 of FIG. 4). The throughput remains low for all ions even when the FAIMS apparatus is employed as a passive transmission device by ceasing to apply the FAIMS dispersion voltage (DV) and compensation voltage (CV), thereby changing its operating mode to "non-dispersive" whereby the FAIMS apparatus acts as a passive device that non-selectively transmits all ions. The low throughput associated with conventional FAIMS apparatuses can lead to an unacceptable Limit of Detection (LOD) of detection and limit of quantitation (LOQ) for assays performed by the mass spectrometer to which the FAIMS apparatus is coupled.

A prior solution to these limitations associated with the use of a FAIMS apparatus as a pre-filter for a mass spectrometer has been to either physically remove an existing FAIMS apparatus from a mass spectrometer that is to perform data-dependent acquisition or to employ, for data-dependent acquisition, a separate mass spectrometer that is not coupled to a FAIMS apparatus. Clearly, such measures are neither time-effective nor cost-effective. Thus, there is a need in the art to be able to realize the filtering advantages of FAIMS during an LC-FAIMS-MRM analysis while also maintaining an adequate number of mass spectral samples for precursor/product ion pair of interest. In a related fashion, there is a need in the art to be able to realize the filtering advantages of FAIMS during the execution of general mass spectral data-dependent acquisition analyses while also maintaining adequate mass spectral limits of detection and quantitation. The present invention addresses these needs.

SUMMARY

To address the above-described needs in the art, the inventors describe, in this disclosure, features of second-generation FAIMS apparatuses which can be coupled with a mass spectrometer, thereby enabling "intelligent" MRM data-dependent acquisition techniques and other analysis techniques that can analyze significantly more isolations per second than would be otherwise possible in a LC-FAIMS-MS apparatus. The above-described limitations associated with a conventional FAIMS coupled to a mass spectrometer can be avoided with the new generation FAIMS devices such that the FAIMS analyzer no longer restricts ion current when situated between an ESI ion source and the MS inlet. Thus, the novel FAIMS apparatuses can be operated in a "non-dispersive" mode (for example, both CV and DV OFF or with a symmetric voltage waveform or an asymmetric waveform of low amplitude) according to which the FAIMS device acts as annular ion transport channel and yields sensitivity nearly identical to having no FAIMS device between the ESI and MS inlet. This feature provides the option to "intelligently" apply the ion filtering function of FAIMS (i.e., the function provided in "dispersive" mode operation) along analyte-eluting regions of the LC gradient. Using such second-generation FAIMS apparatus, a survey mass spectrum can be obtained without any alteration to LC-FAIMS-MS hardware. Using such a second-generation FAIMS apparatus in "non-dispersive" mode, all ion species may be delivered to a coupled mass spectrometer without bias and in sufficient quantities so as to enable generation of survey mass analyses similar to those which may be obtained with a conventional LC/MS system. After such a survey, the FAIMS may be set to an "on" operating mode in which ions can be selectively filtered according to their mobility behavior within the FAIMS apparatus.

According to a first aspect of the present teachings, there is provided a method of operating a system comprising a chromatograph operable to separate sample solutions into fractions, an ion source operable to ionize components of the fractions and a mass spectrometer operable to detect the ions, wherein the method comprises: (a) providing a list comprising respective entries for each of two or more precursor ion species of interest comprising respective precursor-ion m/z ratios; (b) performing a first analysis of a sample comprising: (b1) separating the sample into sample fractions using the chromatograph; (b2) generating a plurality of fraction ion species from each fraction using an ion source; (b3) transmitting the plurality of fraction ion species through an ion mobility spectrometer operated in non-dispersive mode to the mass spectrometer; and (b4) detecting an ion abundance at each of a plurality m/z ratios within each fraction using the mass spectrometer; (c) identifying, from the first analysis, a respective ion-signal-acquisition time (AT) and a corresponding loss-of-ion-signal time (LT), for each m/z ratio that corresponds to a precursor-ion m/z ratio, wherein each AT and LT is referenced to a first-analysis start time taken as time zero; and (d) performing a second analysis of the sample comprising: (d1) establishing a second analysis start time taken as time zero for referencing time periods during the second analysis; (d2) separating the sample into second sample fractions using the chromatograph; (d3) generating a respective plurality of second-sample-fraction ion species from each second sample fraction using the ion source and inletting each plurality of second-sample-fraction ion species to the ion mobility spectrometer; and (d4) for each precursor-ion species of interest for which the respective m/z ratio corresponds to a respective identified AT and LT: (i) operating the ion mobility spectrometer, during a time period occurring at or after said respective identified AT and at or before said respective identified LT, in dispersive mode such that ions of said each precursor-ion species are preferentially transmitted through the ion mobility spectrometer to the mass spectrometer; (ii) fragmenting the preferentially transmitted ion species in the mass spectrometer so as to generate product ions; and (iii) detecting the product ions using the mass spectrometer.

In accordance with some embodiments, the sub-step (b3) of transmitting the plurality of fraction ion species through an ion mobility spectrometer operated in non-dispersive mode may comprise transmitting said plurality of fraction ion species through a high field asymmetric waveform ion mobility spectrometry (FAIMS) spectrometer. The subsequent operation of the FAIMS spectrometer in dispersive mode may comprise transmitting the precursor-ion species within a gas having a gas flow rate through an annular separation region of the FAIMS spectrometer from an ion inlet port to an ion exit port, wherein the gas flow rate and a flow path length between the ion inlet and ion exit ports are such that a residence time of the precursor-ion species within the FAIMS spectrometer is less than or equal to 10 milliseconds.

In order to correctly operate the FAIMS spectrometer, the entries of the provided list may include FAIMS operating parameters necessary for causing the FAIMS spectrometer to preferentially transmit the various precursor ion species therethrough. The FAIMS operating parameters may include values for an asymmetric oscillatory dispersion voltage (DV) and a non-oscillatory compensation voltage (CV) to be applied across electrodes of the FAIMS spectrometer. Such operating parameters may vary according to the particular ion species to be preferentially transmitted through the FAIMS spectrometer.

In some embodiments, the operation of the FAIMS spectrometer in non-dispersive mode may comprise transmitting the ion species therethrough in the absence of application of both the CV and the DV to the electrodes. In some other embodiments, the operation of the FAIMS spectrometer in non-dispersive mode may comprise transmitting the ion species therethrough during the application of a symmetric oscillatory waveform to the electrodes. In some instances, ion species of interest may co-elute; in other words, either the ion-signal-acquisition time (AT) or the loss-of-ion-signal time (LT) corresponding to a first m/z ratio may occur between the AT and LT corresponding to a second m/z ratio. In such instances, the sub-steps (i)-(iii) of sub-step (d4) listed above may repeat or iterate such that the method causes alternating (or cycled) transmission and fragmentation of ions of each m/z ratio.

According to another aspect of the present teachings, there is provided a method of operating a system comprising a chromatograph operable to separate sample solutions into fractions, an ion source operable to ionize components of the fractions and a mass spectrometer operable to analyze and detect the ions, wherein the method comprises: (a) providing an abundance threshold value and a list comprising respective entries for each of two or more precursor ion species of interest comprising respective precursor-ion m/z ratios; (b) transmitting a first portion of a sample fraction comprising a plurality of sample-fraction ion species through an ion mobility spectrometer to the mass spectrometer, wherein the ion mobility spectrometer is operated in a non-dispersive mode; (c) detecting a respective ion abundance at each of a plurality of sample-fraction m/z ratios using the mass spectrometer; and (d) upon detection of an above-threshold ion abundance at a sample-fraction m/z-ratio corresponding to a first one of the precursor ion species of interest: (d1) inletting a second portion of the sample fraction into the ion mobility spectrometer, wherein the ion mobility spectrometer is operated in dispersive mode such that ions of the first precursor-ion species are preferentially transmitted through the ion mobility spectrometer to the mass spectrometer; (d2) fragmenting the preferentially-transmitted ions so as to generate a first set of product ion species; and (d3) detecting the first set of product ion species using the mass spectrometer.

In accordance with some embodiments, the step (b) of transmitting the first portion of the sample fraction through an ion mobility spectrometer may comprise transmitting said first portion of the sample fraction through a high field asymmetric waveform ion mobility spectrometry (FAIMS) spectrometer. The subsequent operation of the FAIMS spectrometer in dispersive mode may comprise operating the FAIMS spectrometer under application of an asymmetric oscillatory dispersion voltage (DV) and a non-oscillatory compensation voltage (CV) across electrodes of the FAIMS spectrometer, wherein said applied DV and CV are chosen so as to preferentially transmit ions of the first precursor ion species through the FAIMS spectrometer. Additionally, the operation of the FAIMS spectrometer in dispersive mode may comprise transmitting the first precursor-ion species within a gas having a gas flow rate through an annular separation region of the FAIMS spectrometer from an ion inlet port to an ion exit port, wherein the gas flow rate and a flow path length between the ion inlet and ion exit ports are such that a residence time of the first precursor-ion species within the FAIMS spectrometer is less than or equal to 10 milliseconds.

In some embodiments, the operation of the FAIMS spectrometer in non-dispersive mode may comprise transmitting the ion species therethrough in the absence of application of both the CV and the DV to the electrodes. In some other embodiments, the operation of the FAIMS spectrometer in non-dispersive mode may comprise transmitting the ion species therethrough during the application of a symmetric oscillatory waveform to the electrodes. The FAIMS operating parameters, including the CV and DV values required to preferentially transmit various ion species may be provided in the list entries. Further, various mass spectrometer operating parameters may be provided in the list entries.

The execution of the above-listed steps (d2) and (d3) may be held conditional upon the continued above-threshold detection of ions at the m/z ratio corresponding to the first precursor ion species of interest immediately after the ion mobility spectrometer is changed to dispersive operation in step (d1). If the abundance at the m/z ratio corresponding to the first precursor ion species of interest should be below the threshold value immediately after the ion mobility spectrometer is changed to dispersive operation, then the corresponding m/z ratio may be added to a list of m/z ratios to be temporarily excluded from fragmentation (an exclusion list) Likewise, the execution of steps (d1) through (d3) listed above may be held conditional upon the m/z ratio corresponding to the first precursor ion species of interest being absent from such an exclusion list.

BRIEF DESCRIPTION OF THE DRAWINGS

The above noted and various other aspects of the present invention will become apparent from the following description which is given by way of non-limiting example only and with reference to the accompanying drawings, not drawn to scale, in which.

DETAILED DESCRIPTION OF EMBODIMENTS

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 1, 2, 3, 4, 5A, 5B, 6, 7A, 7B, 7C, 8, 9, 10A, 10B, 11, 12, 13 and 14 taken in conjunction with the following description.

FAIMS Apparatus Considerations

For purposes of the present discussion, reference may be made to various operating modes of a FAIMS apparatus. When the FAIMS operating mode is set to "non-dispersive" (noted simply as "off" in the attached drawings), the FAIMS apparatus acts as a passive device that non-selectively transmits all ions. One means to implement such a "non-dispersive" operating mode is to cease application of the FAIMS dispersion voltage (DV) and compensation voltage (CV) to the FAIMS electrodes that define a FAIMS analytical gap. Other alternative means of implementing the FAIMS "non-dispersive" mode are also possible. For example, voltage may continue to be applied across the FAIMS electrodes but the applied voltage may configured with a reduced amplitude that is insufficient to cause FAIMS separation or may be changed from its usual asymmetric form to a symmetric voltage form (such as a sinusoidal or sawtooth voltage). Similarly, a FAIMS "on" operating mode may be defined in which DV and CV are applied to the FAIMS electrodes so as to cause the FAIMS apparatus to transmit certain selected ion species therethrough while neutralizing others.

For purposes of this discussion, it is convenient to further recognize different configurations of the "on" operating mode, such as "on m1", "on m2", "on m3", etc., where "m1", "m2", "m3", etc. represent certain analyte ion species. Thus, for example, "on m1" represents a FAIMS operating mode in which the applied DV and CV are such that ion species having ion mobility properties corresponding to the ion mobility properties of the analyte ion species m1 are transmitted completely through the FAIMS apparatus while other ion species are neutralized and eliminated. Thus, when the operating mode of the FAIMS apparatus is "on m1", the ion species m1 species, if present, will be transmitted through the FAIMS apparatus and most other (but possibly not all) ion species will be prevented from passing completely through the FAIMS apparatus. The other operating modes, "on m2", "on m3" are defined similarly, mutatis mutandis.

Figure 5A:
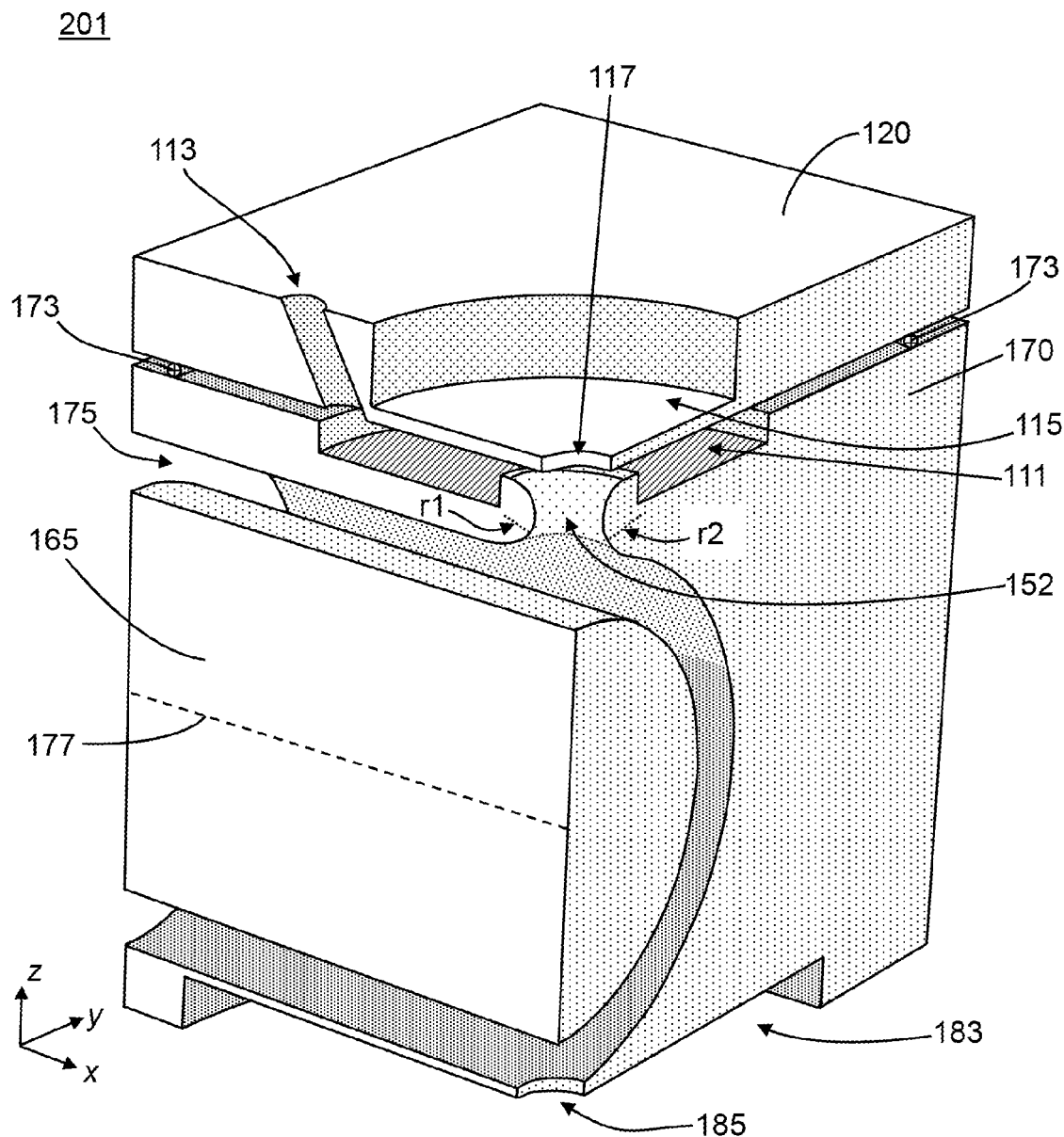
FIG. 5A illustrates a doubly-cutaway perspective view of a FAIMS apparatus in accordance with the present teachings.
Figure 5B:
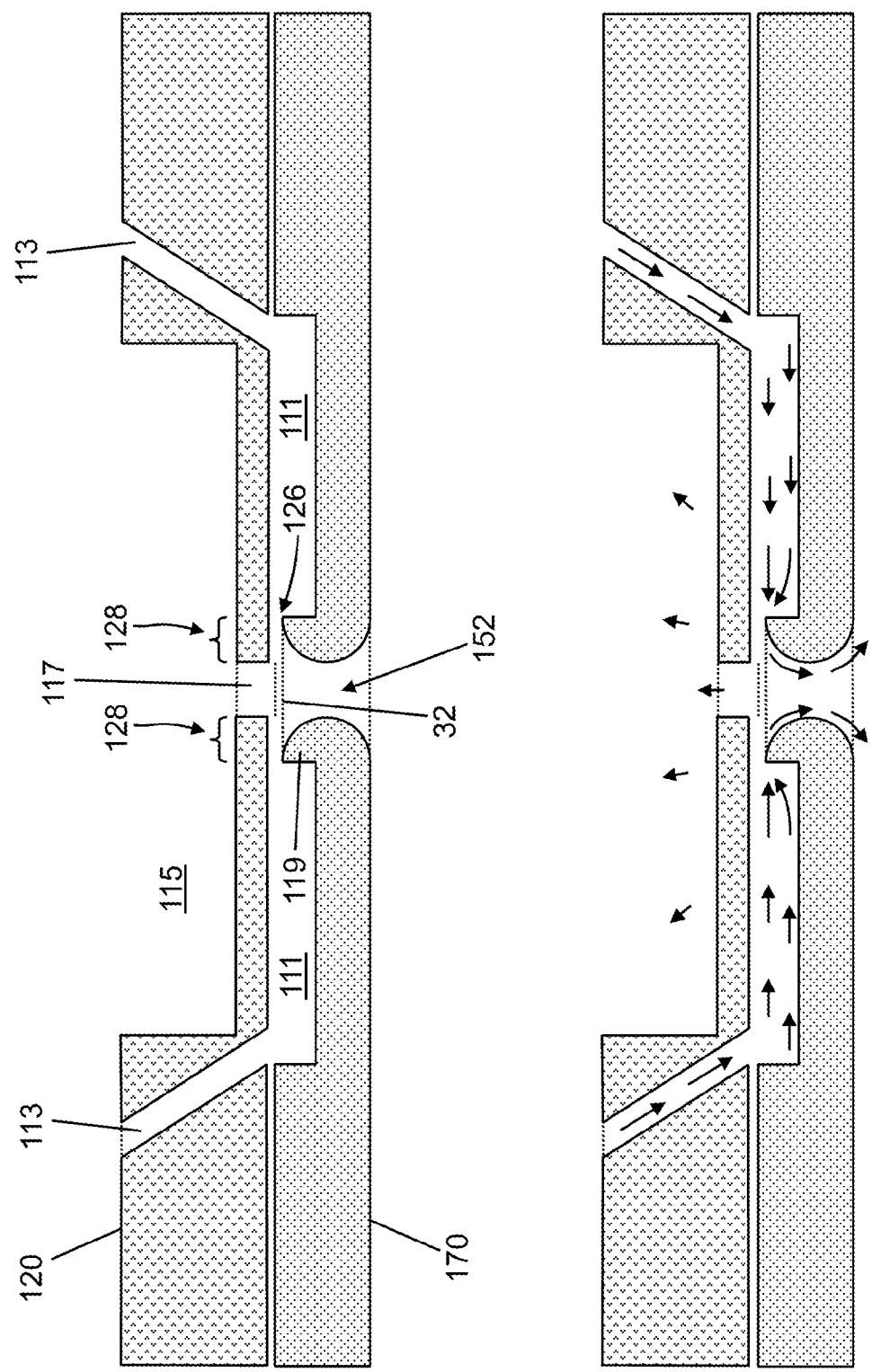
FIG. 5B illustrates a cross-section view (both upper and lower diagrams) of the entrance plate and a portion of the outer electrode of the FAIMS apparatus of FIG. 5A and schematically illustrates flow vectors (lower diagram) within the gas expansion chamber of the apparatus.

FIG. 5A illustrates a perspective sectional view (a quarter section view) of a modified FAIMS apparatus 201 as recently described in U.S. Pat. No. 8,664,593 which is assigned to the assignee of the present invention. The illustration in this figure is doubly-cutaway view that is cut away in a plane (the x-z plane) that includes the cylindrical axis 177 of the FAIMS inner electrode 165 and is also cut away in a plane (the y-z plane) that is perpendicular to the cylindrical axis 177. Each such sectional plane bisects the overall FAIMS apparatus 201 and, thus, the view shown in FIG. 5A is a quarter-section view. FIG. 5B illustrates a cross-section view (both upper and lower diagrams of FIG. 5B) of the entrance plate and a portion of the outer electrode of the FAIMS apparatus of FIG. 5A. FIG. 5B also schematically illustrates (lower diagram only) flow vectors within the gas expansion chamber 111 of the apparatus 201.

Many of the elements of the FAIMS apparatus 201 are similar to corresponding elements in other FAIMS apparatuses previously described herein. However, the FAIMS apparatus 201 differs from previously-described apparatus with regard to the configuration of the ion inlet orifice 152, the gas expansion chamber 111 and the relationship between the inlet orifice 152 and the gas expansion chamber 111. As shown, the apparatus 201 also includes a desolvation chamber 115 recessed into the entrance plate 120 and surrounding the entrance plate aperture 117.

In contrast to apparatuses previously described herein, the expansion chamber 111 of the apparatus 201 forms a recess within the entrance plate 120 in a fashion so as to circumferentially surround the ion inlet orifice 152. Further, the expansion chamber recess is provided such that a portion of the walls of the ion inlet orifice 152 protrudes into the expansion chamber 111 so as to form a ring 119 that circumferentially surrounds a portion of the ion inlet orifice 152. The space between the entrance plate 120 and the inlet end 32 of the ion inlet orifice comprises a narrow gap 126 between the entrance plate and the inlet end of the ion inlet orifice. The entrance plate 120 is configured such that an overlap portion 128 of a face of the entrance plate that bounds the expansion chamber 111 extends beyond the expansion chamber so as to also face the ring portion 119 of the walls of the ion inlet orifice 152.

As a result of the configuration shown in FIGS. 5A-5B, gas that enters the expansion chamber 111 through gas conduits 113 is caused to flow around the circumference of the ring 119 and then to flow into and through the gap 126. The apparatus 201 is configured such that the width of the gap 126 is significantly less than the width of the expansion chamber 111, wherein the width of the gap is measured between the entrance plate 120 and the inlet end 32 of the ion inlet orifice 152 and the width of the chamber 111 is measured between the facing surfaces of the entrance plate 120 and the outer electrode 170 that bound the chamber. Because of these different widths, the gas pressure and flow velocity are both caused to increase as the gas flows into the gap. The increased-velocity gas flow then enters the inlet end 32 of the ion inlet orifice 152 through the entirety of the gap 126 that circumferentially surrounds the inlet end of the ion inlet orifice 152. Ions pass through the aperture 117 in the entrance plate and then cross the gap 126 and pass into the ion inlet orifice 152 where they are entrained in the gas flow. The overlap portion 128 of the entrance plate confines the gas to the gap 126 and enables the increase in the gas flow velocity. The increased gas flow velocity and orifice wall curvature enable the Coandă effect within the analytical gap 175. The wall curvature also plays an important role in delaying "flow separation" such that the gas streamlines remain attached to the outer electrode surface within the analytical gap.

As is illustrated in the lower portion of FIG. 5B, the increased gas flow velocity produced by the squeezing of the gas flow into the gap 126 causes a high-velocity jet to form against the convexly curved interior walls of the ion inlet orifice 152, thereby causing the high velocity gas to follow the curved surface of the walls in accordance with the Coandă effect. Thus, as previously discussed in regard to the apparatus 109 shown in FIGS. 2-3, the high velocity gas flow (and, consequently, the majority of the gas itself) is diverted into the analytical gap 175 so as to avoid impact with the inner electrode 165. The majority of the entrained ions are carried along with the gas, thereby improving the ion throughput through the FAIMS apparatus.

The curvature of the interior walls of the ion inlet orifice 152 of the FAIMS apparatus 201 (FIG. 5A) differs from the curvature of the walls of the inlet orifice 151 of the FAIMS apparatus 109 (FIGS. 2-3) in that the walls of the inlet orifice 152 comprise different radii of curvature in different cross sections. In the x-z cross section taken parallel to the cylindrical axis 177 of the inner electrode, the radius of curvature is of the wall is $r_1$ whereas, in the y-z cross section oriented perpendicular to the axis 177, the radius of curvature is $r_2$, where $r_1 \neq r_2$. In some embodiments, the radius $r_1$ may approach infinity such that the wall of the ion inlet orifice 152 is not curved (i.e., is a straight line) in the bisecting x-z plane containing the cylinder axis 177. Other configurations may cause the ion inlet orifice to have an oval-shaped, elliptical-shaped, or eye-shaped configuration or projected shape as viewed through the orifice and as illustrated in the upper diagrams of FIGS. 7A-7B and as discussed further below.

The reason for the difference in the wall curvature of the ion inlet orifice 152 in different directions is that, in the y-z plane, the required deflection of the gas jet parallel to the y-axis is greater than the amount of deflection that that is either necessary or desirable parallel to the x-axis or in the x-z plane. The greater degree of deflection required in the y-z plane is a simple result of the geometry of the annular analytical gap 175. For example, consider gas that approaches the ion inlet orifice 152 along the negative-y direction in the expansion chamber 111. In order to be completely diverted into the analytical gap 175, the direction of flow must be diverted so as to have a component vector in the positive y-direction. No such requirement exists for gas that approaches the ion inlet orifice 152 along, for example, the positive-x direction in the expansion chamber 111. In this latter case, the most important requirement is to maintain most of the gas flow within the analytical gap near an axis (not shown) that passes from the ion inlet orifice 152 to the ion exit orifice 185. The smaller radius $r_2$ in the y-z cross section allows the required greater amount of angular deflection of the gas jet to be accomplished sufficiently gradually such that the streamlines do not detach or separate from the curved wall.

The inventors have discovered that the provision of different radii of curvature of the walls of the inlet orifice 152, as illustrated in FIG. 5A, has the effect of confining the bulk of the carrier gas flow—and, consequently, the bulk of the ion flow—within the analytical gap to a narrow ring within the analytical gap 175 surrounding the midpoint of the cylindrical inner electrode 165. The inventors have further discovered that such gas flow confinement may be achieved by fabricating the ion inlet orifice so as to have an oval-, elliptical-, or eye-shaped configuration or shape as viewed through the orifice (that is, as projected onto the x-y plane according to the axes orientation illustrated in FIG. 5A) with the long dimension of the ellipse or "eye" oriented parallel to the cylindrical axis 177 of the inner electrode 165. Examples of such oval-, elliptical-, or eye-shaped ion inlet orifices 153 are illustrated in plan view in FIGS. 7A-7B and in two mutually perpendicular elevation views in FIG. 7C. Note, from FIG. 7C, that the orifice walls remain convexly curved in both the y-z and x-z planes so as to exploit the Coandă effect and that the radii of this curvature in the y-z and x-z planes may be either equal to or different from one another. The oval-shaped ion inlet orifices 153 and the associated gas flow illustrated in FIGS. 7A-7B may be compared to the radially symmetric inlet orifice 151 and its associated gas flow as shown in FIG. 6.

Figure 6:
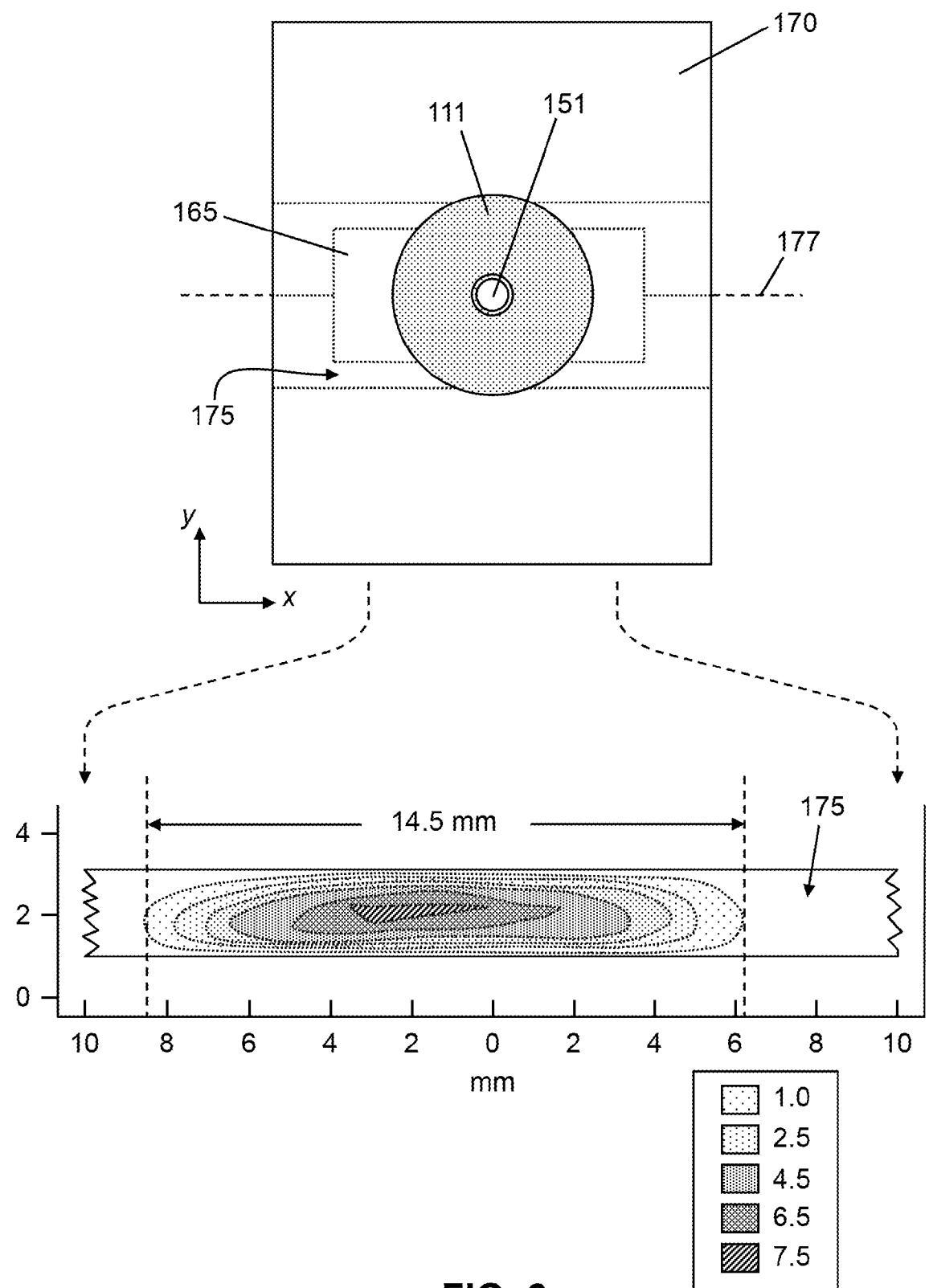
FIG. 6 is (top portion) a plan view of a FAIMS apparatus having a circular ion inlet orifice with internally convexly curved walls and (bottom portion) a plot of calculated flow velocity isopleths within the analytical gap of the FAIMS apparatus.
Figure 7A:
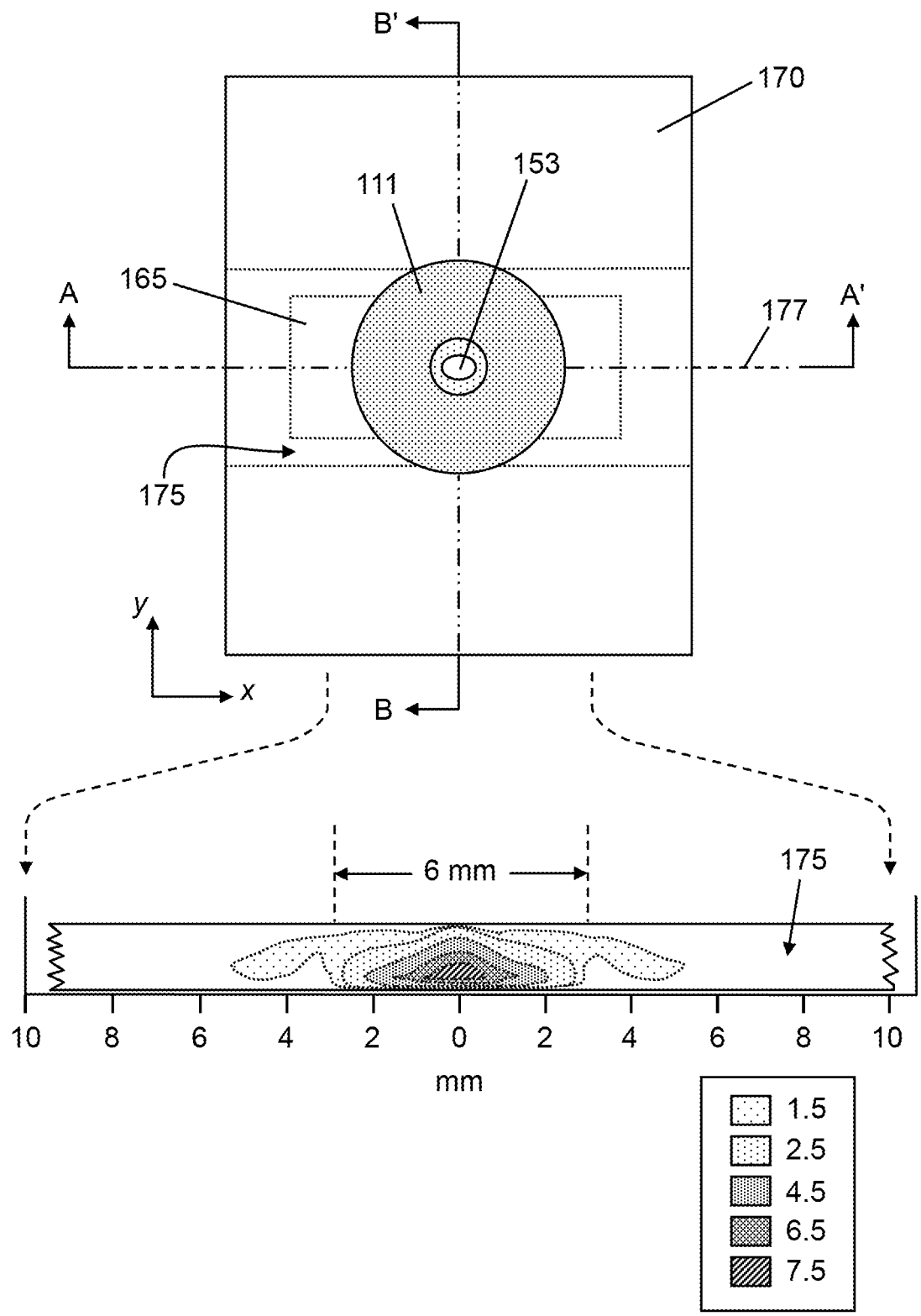
FIG. 7A is (top portion) a plan view of a second FAIMS apparatus that is similar to the apparatus depicted in FIG. 6 except that the ion inlet orifice is oval in shape and (bottom portion) a plot of calculated flow velocity isopleths within the analytical gap of the second FAIMS apparatus.
Figure 7B:
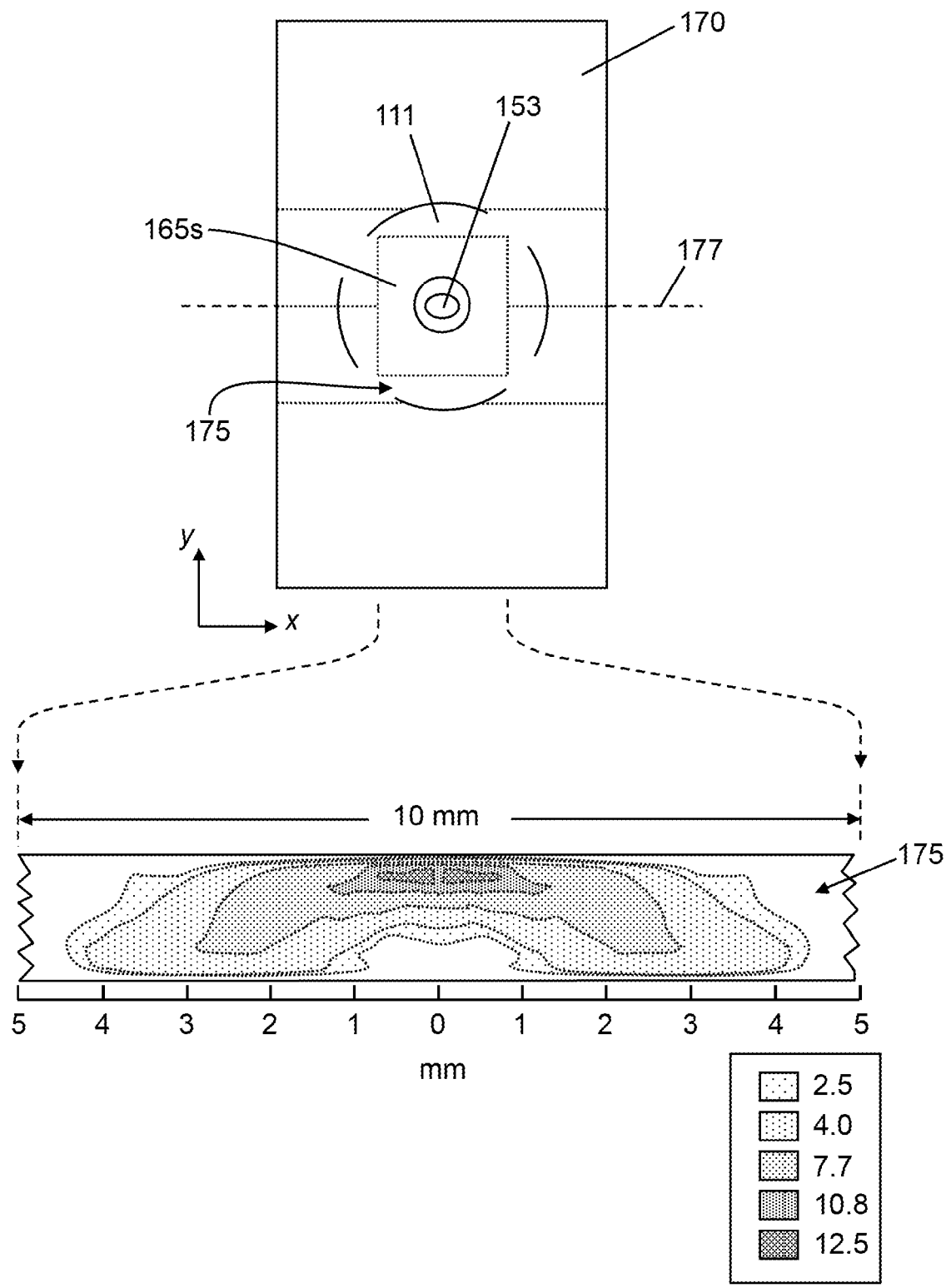
FIG. 7B is (top portion) a plan view of a third FAIMS apparatus that is similar to the apparatus depicted in FIG. 7A except that the length of the inner cylindrical electrode is shortened to 10 mm from 25 mm and (bottom portion) a plot of calculated flow velocity isopleths within the analytical gap of the third FAIMS apparatus.

The effect of providing an oval-, elliptical-, or eye-shaped configuration of the ion inlet orifice 153 may be observed by comparison of FIG. 6 with FIG. 7A, the bottom sections of which show the results of numerical fluid-dynamic gas flow rate calculations taken along an x-y cross sectional plane within the analytical gap. The top portions of FIG. 6 and FIG. 7A are "top views" of the respective apparatus as would be viewed along a line of sight in the negative direction of the respective z-axis in accordance with the orientation shown in FIG. 5A. FIGS. 7A-7B relate to a FAIMS apparatus having the oval-shaped ion inlet orifice 153 (as viewed from the top) with the long dimension of the orifice oriented parallel to the cylindrical axis 177 of the FAIMS inner electrode 165. By contrast, FIG. 6 relates to a FAIMS having the previously described ion inlet orifice 151 that is radially symmetric.

Figure 7C:
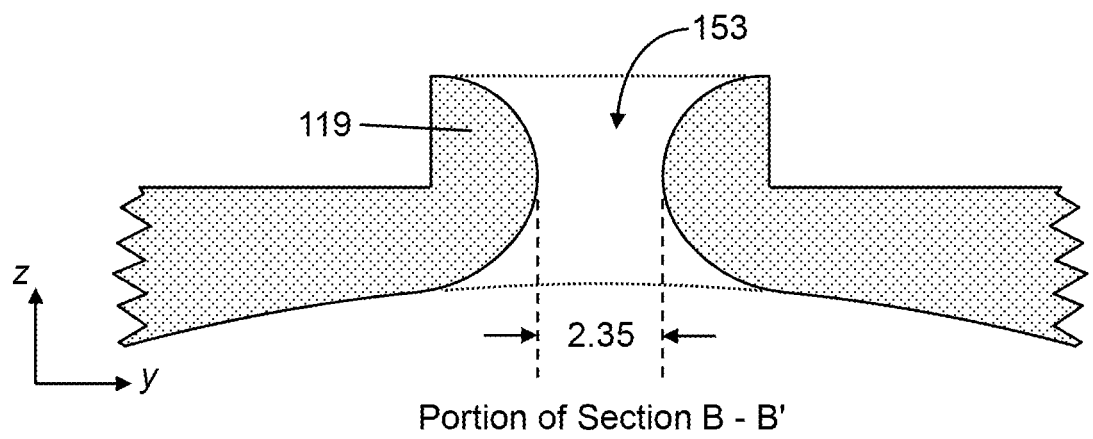
FIG. 7C is a pair of expanded elevation cross sectional views along the sections A-A' and B-B' noted in the upper portion of FIG. 7A, showing the differing dimensions of the ion inlet orifice in the two mutually perpendicular cross sections.
Figure 7C:
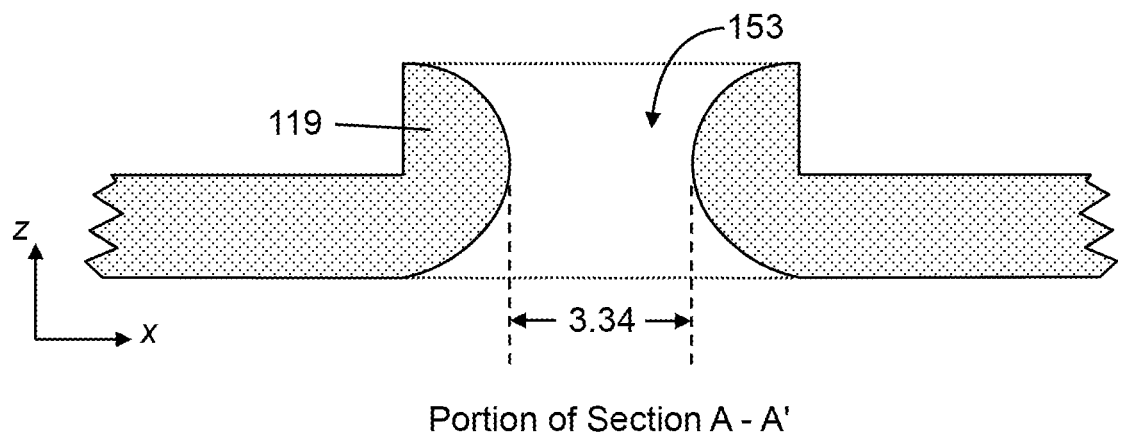

In each of FIG. 6, FIG. 7A and FIG. 7B, the axis 177 of the cylindrical rod-like inner electrode 165 is shown. Also shown in phantom (with dotted lines) in the upper diagram of each of FIGS. 6, 7A and 7B are a cross-section of the inner electrode 165 and the analytical gap 175 as taken in a horizontal plane (parallel to the plane of the page) that contains the axis 177. The lower portion of each of these figures is an expanded view of the analytical gap 175 within this same cross sectional plane with superimposed patterned regions, each bounded by an isopleth representing one of various calculated gas flow velocities. The legend in each of FIGS. 6, 7A and 7B correlates the particular patterns within each isopleth to the approximate flow velocity (in msec) represented by the respective isopleth. FIG. 7C shows a pair of expanded cross sectional views, in the y-z plane and in the x-z plane, as defined in FIG. 5A, of the ion inlet orifice 153 and surrounding ring 119 showing the dimensions (in mm) of the orifice and the wall curvature in the two cross sections. The two cross-sectional views in FIG. 7C represent portions of the sections A-A' and B-B' whose positions are noted in the upper portion of FIG. 7A. The length of the inner electrode, as shown in FIG. 6, is set at its conventional value of 25 mm.

The results of the gas flow rate calculations, as shown in the lower portion of FIG. 6, indicate that a large proportion of the total gas flux is spread out within a zone of the analytical gap extending for a distance greater than 10 mm parallel to the inner electrode axis 177. Because the ion inlet orifice 151 shown in FIG. 6 is radially symmetric with a non-varying convex wall curvature between the orifice inlet end 32 and the orifice outlet end 33 (see inset 30 of FIG. 2), the inventors reason that the Coandă effect causes gas flux vector components directed away from the orifice along that are roughly equal along both the x and y axes (see FIG. 5A). Although diversion of the gas and ion flow away from the inner electrode 165 is desirable in order to prevent unwanted neutralization of ions at the electrode surface, diversion of the gas and ions in a direction parallel to the electrode axis 177 can cause unnecessary spreading of the gas and ion plume as evidenced by the results in the lower portion of FIG. 6.

The bottom portion FIG. 7A shows results of flow velocity calculations for a non-radially-symmetric ("eye-shaped") ion inlet orifice 153 as depicted in the top portion of FIG. 7A and in FIG. 7C. For this latter configuration, the calculated results show that most (i.e., greater than fifty percent) of the gas flow within the analytical gap 175 is restricted to a zone extending 4 mm to either side of the center of the inner electrode. Evidently the reduced surface area at the two narrow ends of the oval-shaped ion inlet orifice 153 (see upper portion of FIG. 7A and FIG. 7C) decreases the Coandă-effect-related spreading of gas and ion flow away from the center of the inner electrode while the greater surface area of the orifice walls parallel to or sub-parallel to the cylindrical axis 177 of the inner electrode 165 (the x-direction according to the illustrated axes orientation) causes smoother gas flow and greater deflection of the gas streams parallel to the curved outer electrode wall, in accordance with the Coandă effect, that is adequate to divert the flow of gas and entrained ions away from the center electrode.

Because of the lateral restriction of the flow stream as indicated in FIG. 7A, the inventors have performed fluid dynamic calculations relating to and experimental results on a still-further-modified side-to-side FAIMS apparatus having a shorter-length (specifically, 10 mm length) inner electrode 165s and the same oval-shaped ion inlet orifice 153 as described previously herein. A top-view of the apparatus and the results of the fluid flow calculations are shown in the upper and lower portion of FIG. 7B, respectively. Although not identical to the calculated fluid flow regime illustrated in FIG. 7A, the calculated results shown in the lower portion of FIG. 7B indicate that a large proportion of the fluid flow—and, by extension, the ion flow—is maintained within the analytical gap 175 between the outer electrode and the shortened inner electrode. The results of experiments (not shown) verify that ion transmission through the apparatus having the oval inlet orifice 153 and the shorter inner electrode 165s is not significantly degraded compared to an apparatus having a conventional 25 mm long inner electrode.

Because the use of a shortened (10 mm) inner electrode is made possible by the employment of an oval-shaped inlet orifice that has an interior wall that is convexly curved between its inlet and outlet ends, it is possible to fabricate a side-to-side FAIMS apparatus that is smaller in size relative either to a conventional side-to-side FAIMS apparatus (FIG. 1) or to a modified version of that apparatus having, as illustrated in FIG. 7A, a radially symmetric ion orifice with convexly curved walls. The electrodes of the smaller FAIMS apparatus use less metal mass than would otherwise be required, thereby reducing the thermal mass of the inner electrode and the electrical capacitance of the device. The reduced thermal mass of the shortened inner electrode permits more rapid heating and cooling relative to prior FAIMS side-to-side FAIMS apparatuses, thereby facilitating more-rapid control of temperature, which is a known means of controlling FAIMS operation.

The reduced capacitance of the novel FAIMS apparatus described herein enables the use of a higher-frequency asymmetric FAIMS waveform during operation of the apparatus. The use of a higher-frequency asymmetric FAIMS waveform enables a higher gas flow rate to be either pumped through or pulled through the FAIMS apparatus without loss of FAIMS sensitivity. The higher gas flow rate leads to a shorter transit time (residence time) through the side-to-side FAIMS apparatus. Because the ions are carried by the gas flow and because the gas flow is laterally restricted to a region of the analytical gap within a few centimeters of the center of the inner electrode, the higher gas flow rate does not lead to significant loss of ion transmission through such a shortened FAIMS. The inventors have experimentally demonstrated that such an apparatus can achieve a residence time of 10 ms without significant degradation of signal intensity or resolution. In other words, by employing the design considerations described herein, the flow path length through the FAIMS apparatus between ion inlet and ion exit ports can be made sufficiently short and employed with a sufficiently high gas flow rate such that the average time period during which any ion resides within the FAIMS apparatus during its operation (i.e., the residence time) may be less than or equal to 10 milliseconds.

Figure 1:
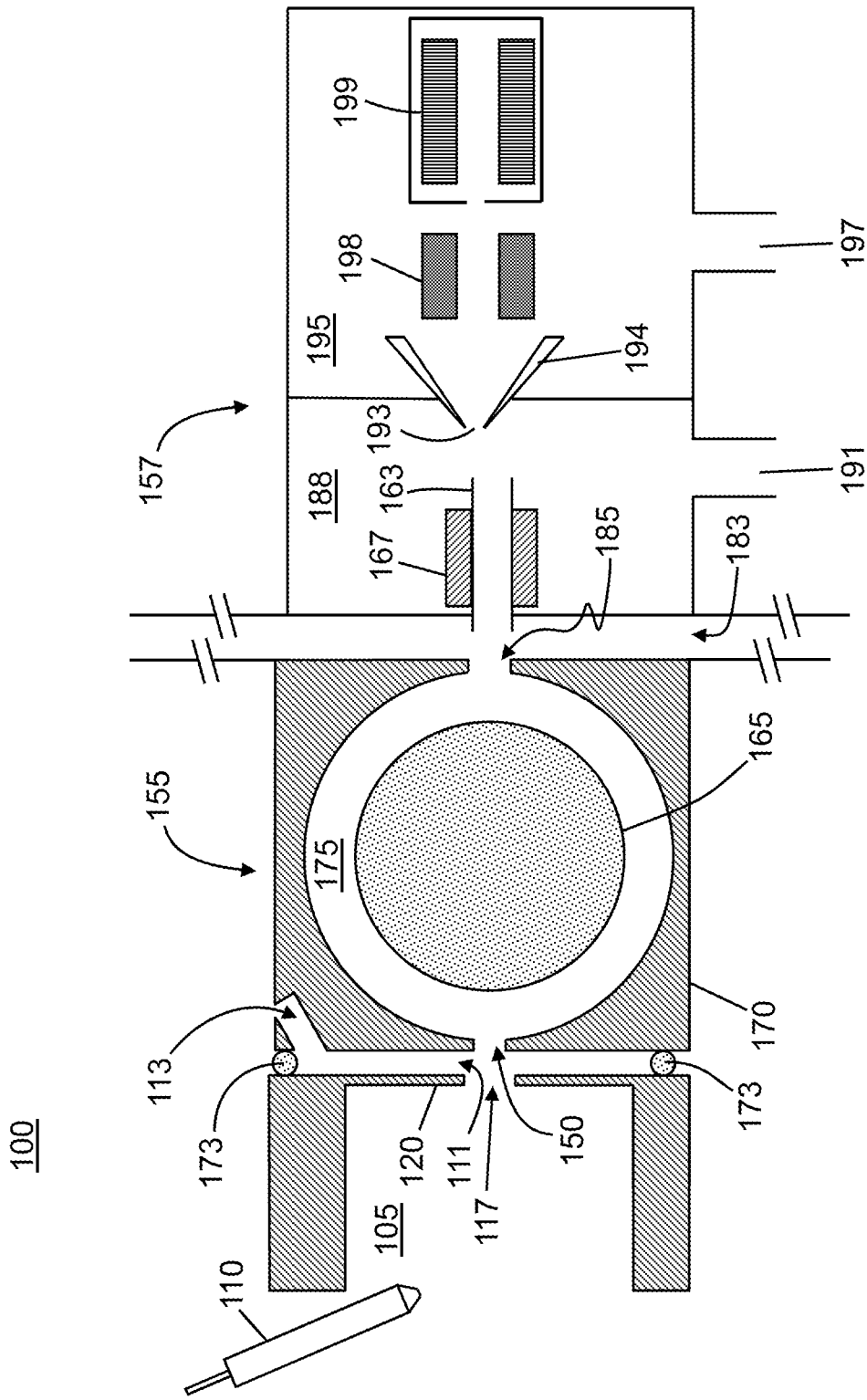
FIG. 1 is a schematic diagram depicting a first known system for analyzing ions including an ion mobility device.
Figure 9:
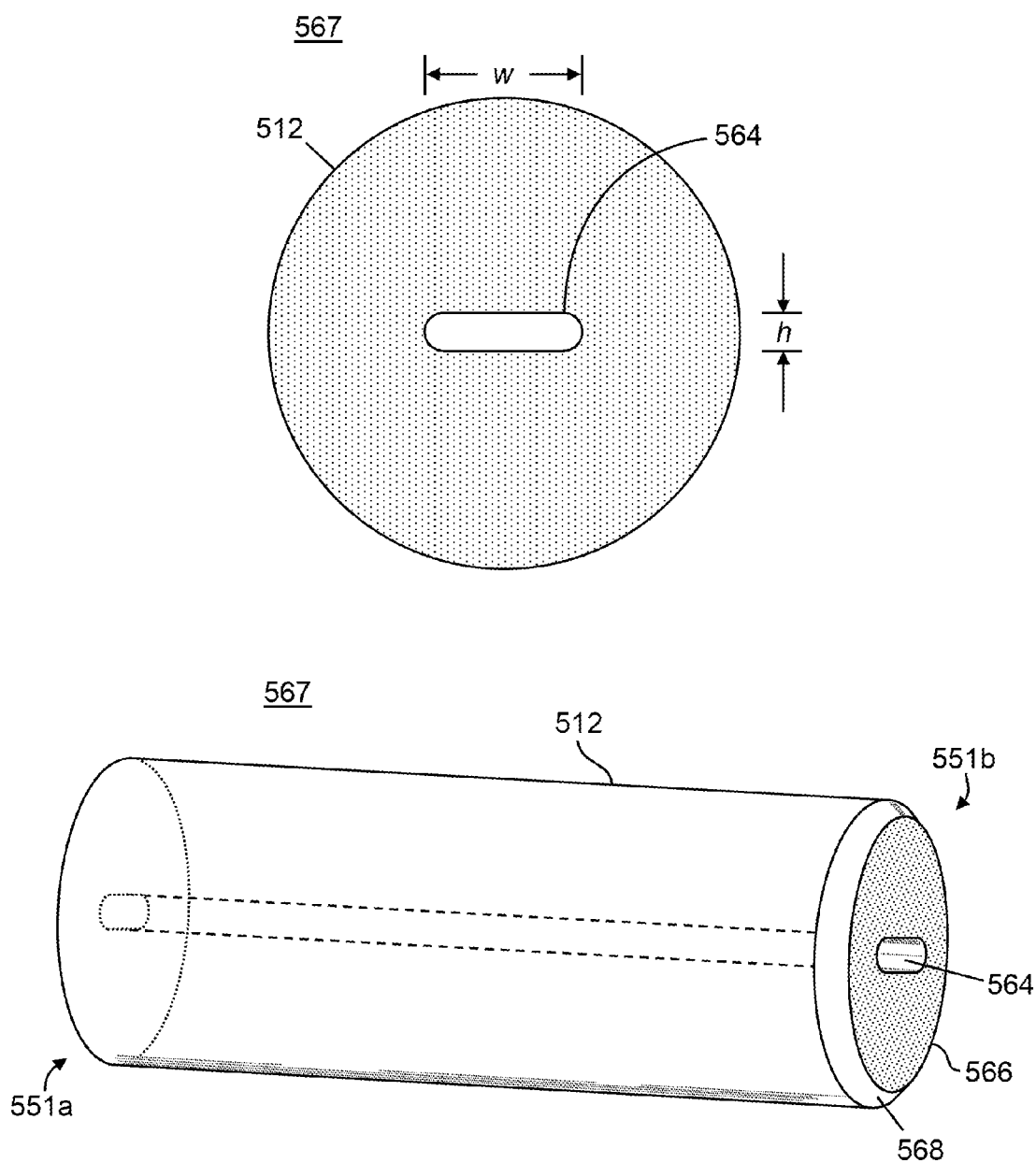
FIG. 9 is a cross sectional and perspective view of a known ion transfer tube that comprises a slotted internal bore and that may be advantageously employed, in accordance with some embodiments, as part of a system comprising a FAIMS apparatus and a mass spectrometer in accordance with the present teachings.

The greater gas flow rate that may be passed through the shortened-inner-electrode FAIMS apparatus (FIG. 7B) could be facilitated, by way of non-limiting example, by the use of greater gas pumping capacity in the FAIMS-MS system 100 illustrated in FIG. 1. A mass spectrometer apparatus employing such greater gas pumping capacity may advantageously employ an ion transfer tube 567, as schematically illustrated in FIG. 9, that comprises a non-circular slot-shaped internal bore 564 that has a bore width, w, that is greater than a bore height, h, and that passes through solid tube member 512 from an inlet end 551a to an outlet end 551b. The upper and lower portions of FIG. 11 respectively show a cross-sectional view and a perspective view of the ion transfer tube 567. The slot-shaped bore 564, may alternatively be referred to as an obround bore or a "letterbox" bore. The outlet end 551b of the ion transfer tube 567 may be terminated by a substantially flat end surface 566 that is substantially perpendicular to the length of the tube and to the flow direction. A beveled surface or chamfer 568 may be used to align and seat the outlet end of the ion transfer tube against a mating structural element within a vacuum chamber of a mass spectrometer. The slotted-bore ion transfer tube 567 provides an advantage, as compared to a conventional round-bore ion transfer tube (e.g., the ion transfer tube 163 illustrated in FIG. 1), in that adequate ion de-solvation may be performed at greater gas flow rates.

Methods for Conducting MRM Analyses with a FAIMS-MS System

Figure 2:
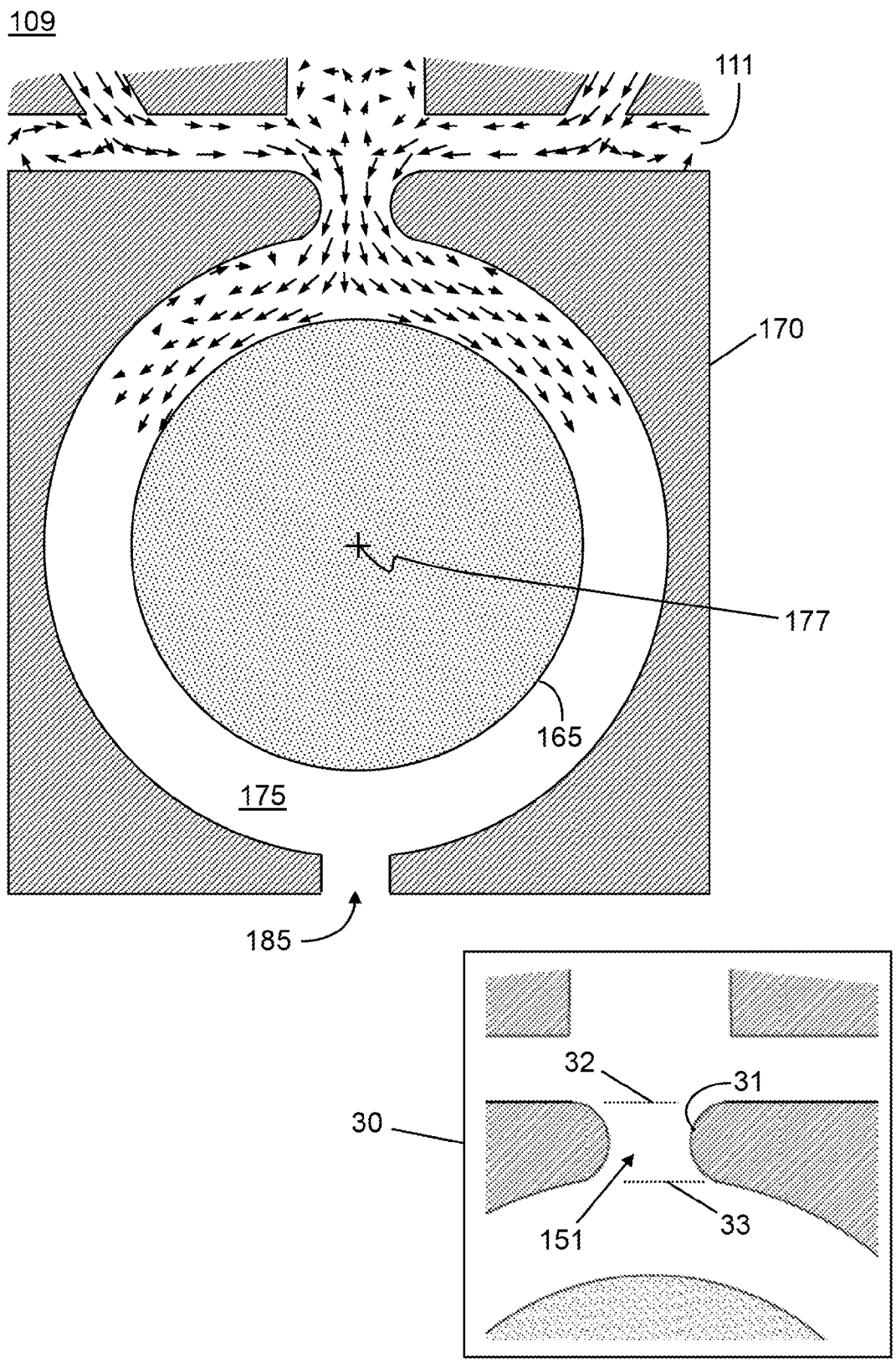
FIG. 2 illustrates gas flow streamlines, as modeled by computational fluid dynamics, through flow channels of a FAIMS apparatus having entrance electrode that is modified so as to exploit the Coandă effect.
Figure 3:
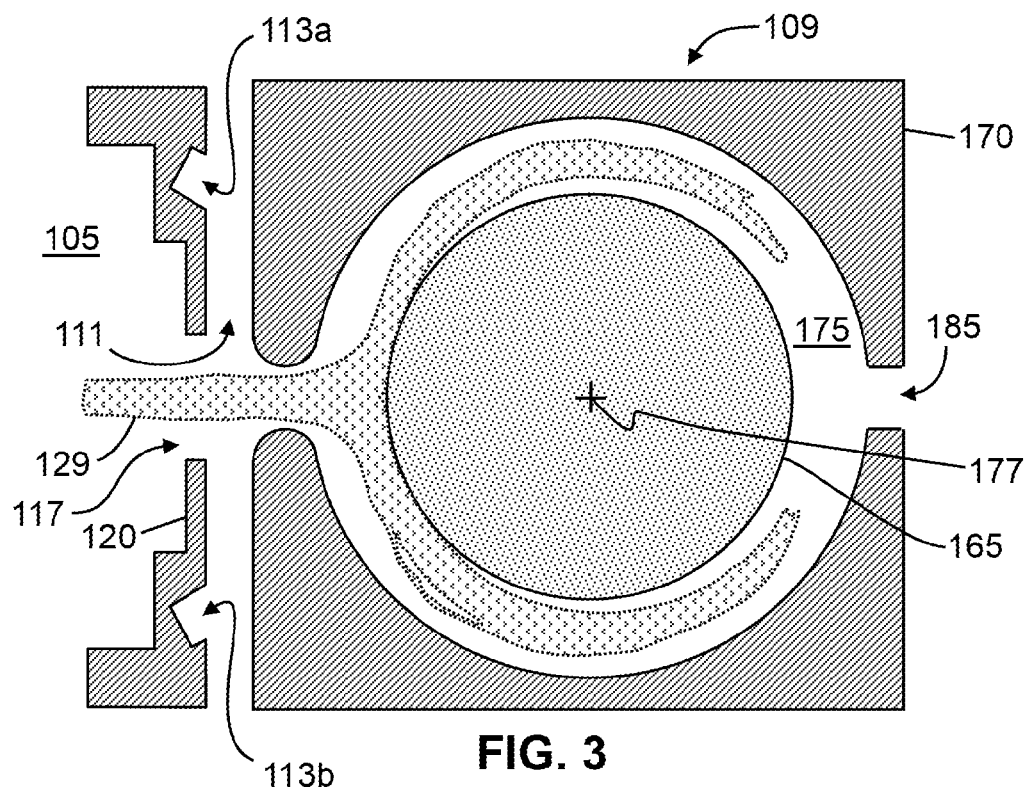
FIG. 3 a simulation of a region of ion flow from an ion source region into and through a side-to-side FAIMS apparatus that is modified so as to exploit the Coandă effect.
Figure 4:
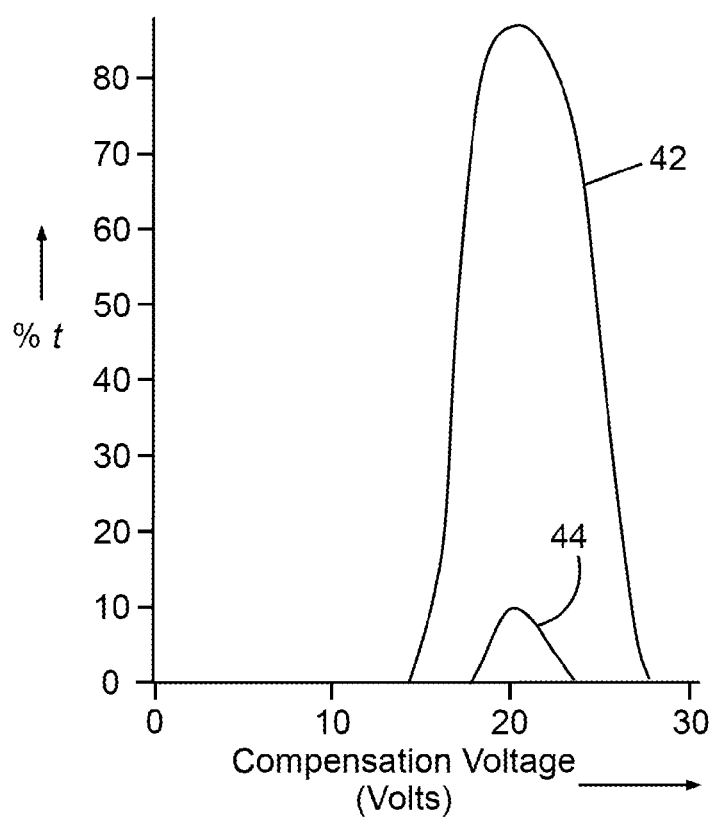
FIG. 4 illustrates a comparison between simulated CV scans corresponding to the FAIMS apparatuses of FIG. 2 and FIG. 3.
Figure 10A:
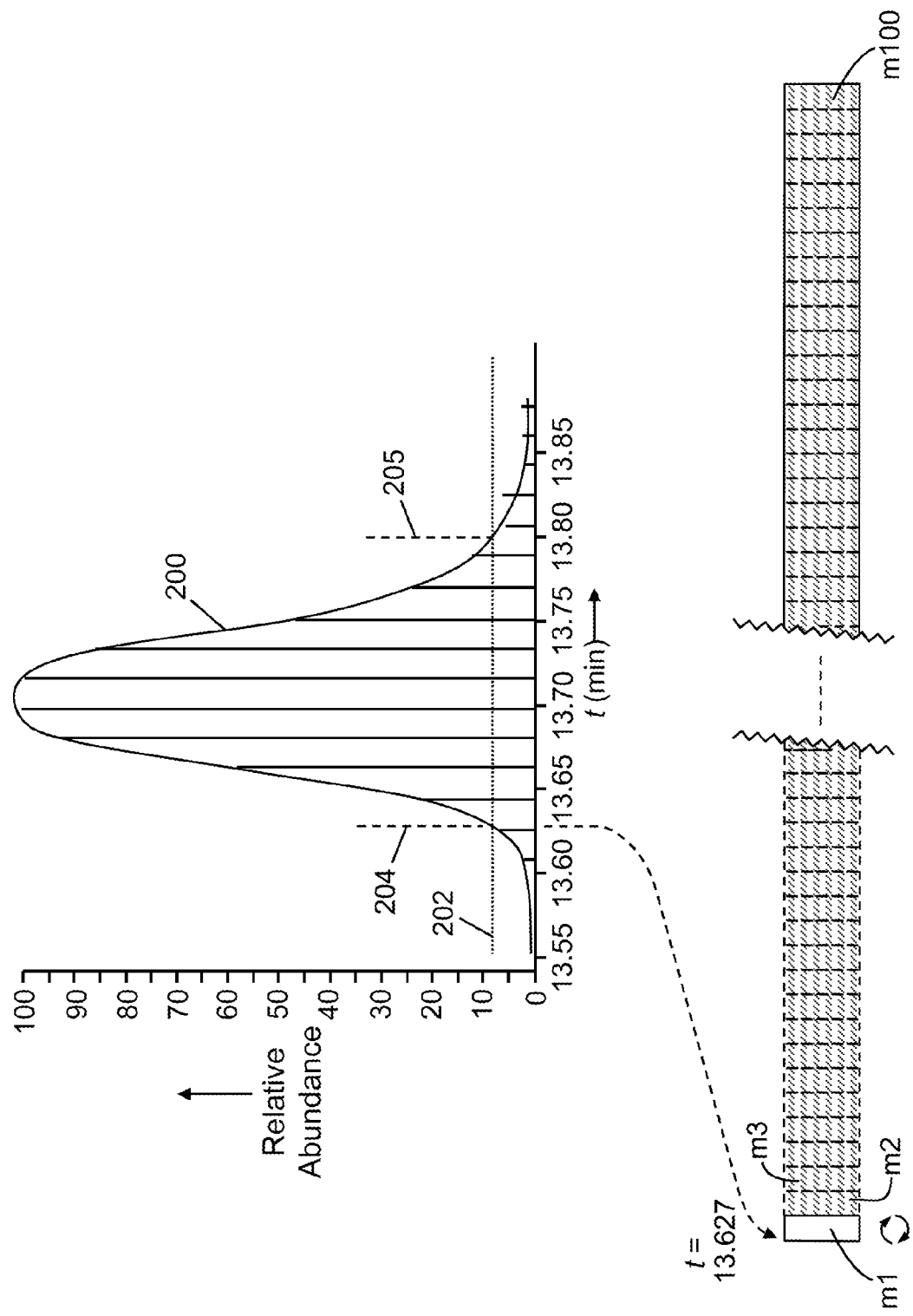
FIG. 10A is a schematic depiction of a sequence of events occurring, in accordance with some embodiments according to the present teachings, during multiple-reaction monitoring during the elution of a single chromatographic peak using a system comprising a FAIMS apparatus coupled to a mass spectrometer.
Figure 10B:
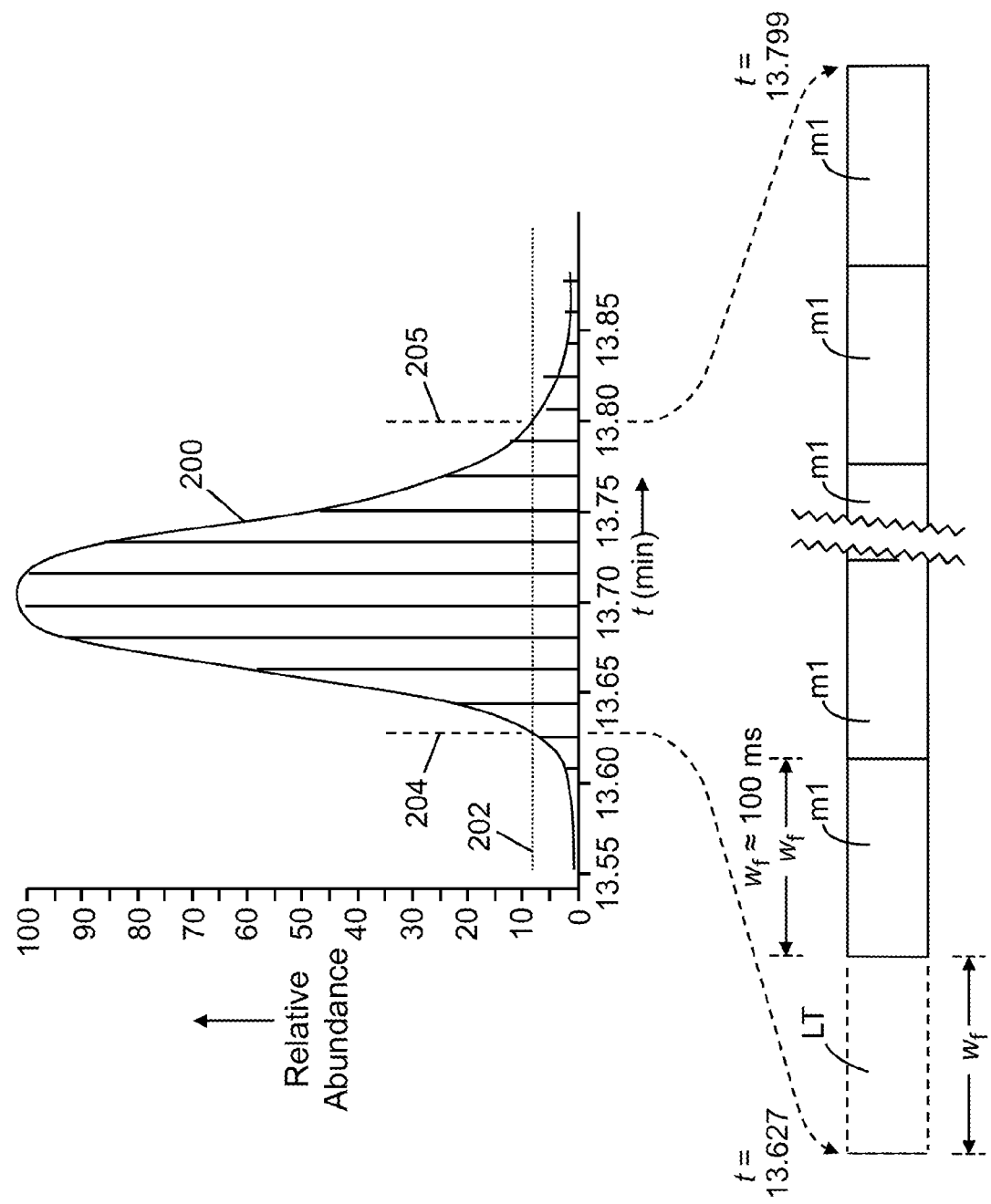
FIG. 10B is an alternative schematic depiction of the sequence of events depicted in FIG. 10A.
Figure 13:
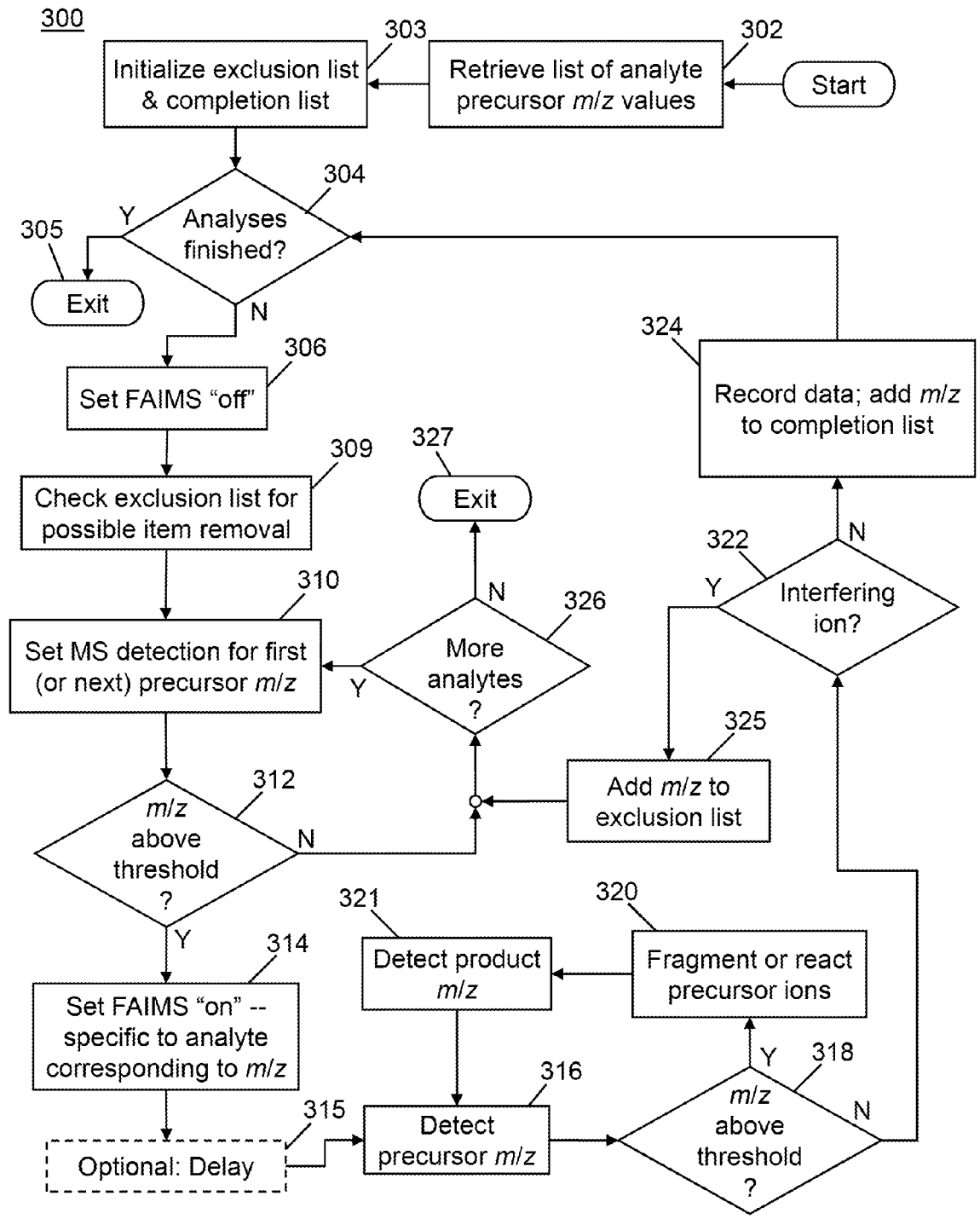
FIG. 13 is a flow diagram of a first method for operating an analytical system comprising a liquid chromatograph, a FAIMS apparatus and a mass spectrometer in accordance with the second teachings.

FIGS. 10A-10B graphically depict and the flowchart of FIG. 13 describes a first method, in accordance with the present teachings, for conducting MRM analyses with a FAIMS-MS system. The method 300 outlined in FIG. 13 and depicted in FIGS. 10A-10B may employ either a FAIMS apparatus having a residence time of approximately 100 ms or more, or a shorter residence time of 10 ms or less, as in the FAIMS apparatus depicted in FIG. 5A and FIGS. 7A-7C, respectively, or a residence time intermediate between these values. Indeed, the method 300 may be utilized in conjunction with any FAIMS apparatus coupled to a mass spectrometer, provided that the transmission throughput of the FAIMS is sufficient for the analysis at hand. Either a FAIMS apparatus having a radially symmetric ion inlet orifice 151 (as illustrated in FIGS. 2-3 and FIG. 6) or a FAIMS apparatus as illustrated in FIGS. 5A, 7A, 7B and 7C can be operated so as to provide high ion throughput and are acceptable for operation using the method 300.

Figure 8:
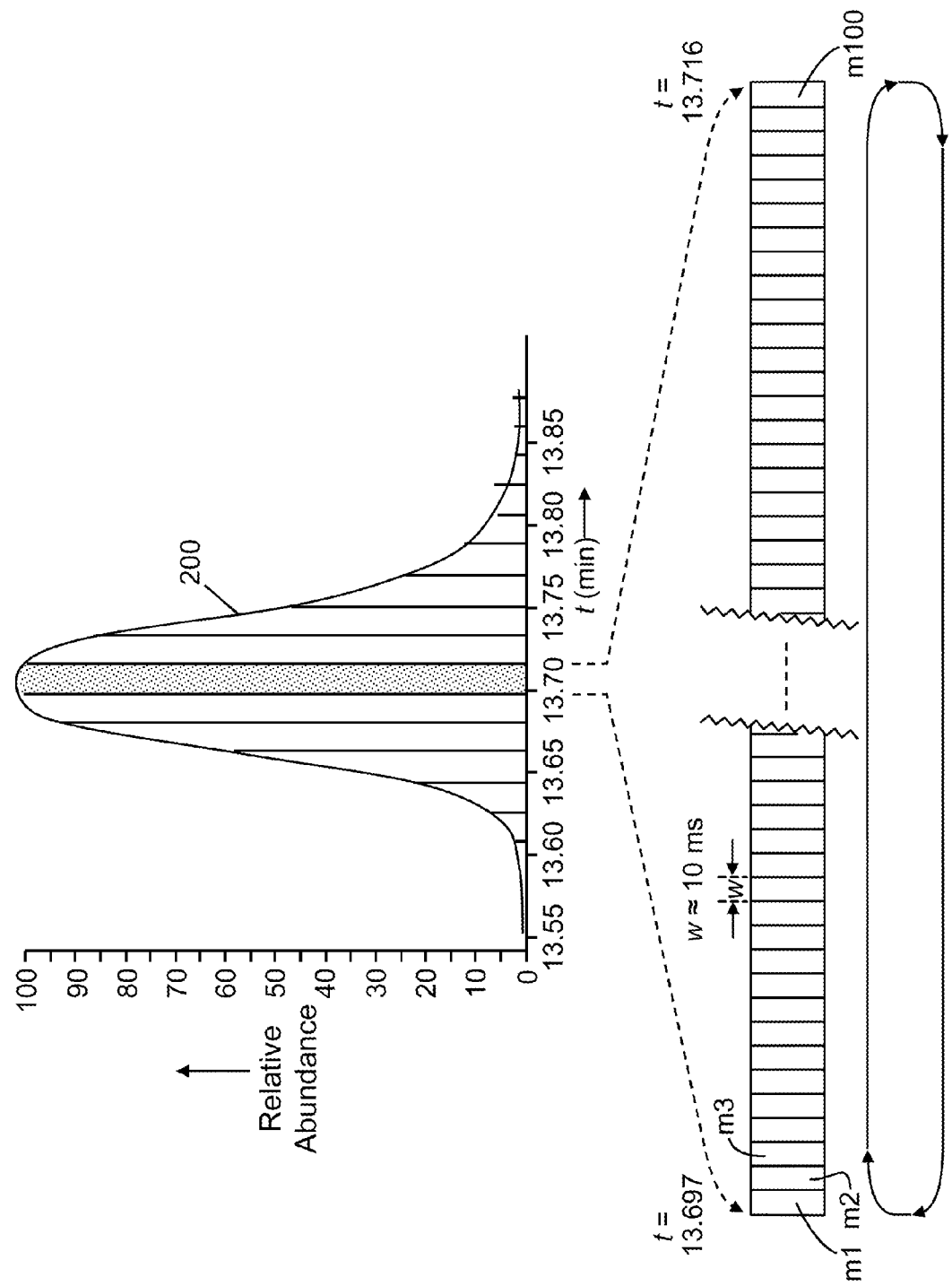
FIG. 8 is a schematic diagram of a typical sequence of events that occur during conventional multiple-reaction monitoring, in a liquid chromatography mass spectrometry system, during the elution of a single chromatographic peak.

Both FIGS. 10A-10B show the same hypothetical chromatographic elution peak 200 as is also shown in FIG. 8. The peak 200 may represent the elution of a single analyte, as represented by a single analyte ion of interest. More generally, the peak 200 may represent the appearance of more than one ion species within the ion stream generated by an ion source where the various ion species represent at least partially overlapping co-elution of more than one analyte species. In this latter situation, it is preferable to employ the alternative method 400 outlined in FIG. 14. Instead, the following discussion relating to the method 300 (FIG. 13) assumes that the peak 200 represents the appearance of a single diagnostic parent ion species (ion species m1, having mass-to-charge ratio of $(m/z)_1$ in the illustrated hypothetical example of FIGS. 10A-10B) and possibly other background or interfering ions that are not of diagnostic interest. Generally, the ion species m1 will be one of a plurality of diagnostic species of interest for which detection and analysis may occur during a single LC-FAIMS-MS experiment. Additional diagnostic parent ions (the ion species m2, m3 . . . m100 in the example) may appear in additional separate elution peaks (not shown in FIGS. 9A-9B) that may occur either prior to or subsequent to the time range indicated for the peak 200. The same method 300 may also be employed in conjunction with the analyses of the ions represented by those additional peaks.

Method 300 (FIG. 13) may begin with a step 302 in which information pertaining to the various diagnostic analyte of species of interest is retrieved or input, either from an electronic storage device are by input from a user. The retrieved information comprises at least a list of respective mass-to-charge (m/z) values, as expected to be generated by an ionization source, of the various analyte species of interest. The retrieved information may further comprise information pertaining to product ion species to be formed by reaction or fragmentation of each respective diagnostic ion species generated by the ion source and may further include mass spectrometer operational parameter settings required to detect or fragment the ions. The list may also include information pertaining to FAIMS settings to be employed in conjunction with the detection of each such ion species. Such FAIMS parameters may include compensation voltage (CV) and dispersion voltage (DV) settings to be used so as to cause the FAIMS apparatus to transmit each respective diagnostic ion species completely through the FAIMS apparatus to the mass spectrometer while simultaneously neutralizing and eliminating other ion species.

In step 303 of the method 300 (FIG. 13), two internal logical lists are created and initialized so as to be empty. The dynamic exclusion list is a listing of ion species (generally, as represented by their m/z values) that are to be temporarily excluded from detection. The completion list is a list of ion species which have been analyzed during an experimental run and which will not be further detected or quantified during the experimental run. As an alternative to using a formal completion list, information pertaining to an ion species may be simply deleted from the list of species to be analyzed as the analysis of the species is completed.

The subsequent steps 304-324 of the method 300 comprise an iterated loop of steps. During each iteration, a determination is made (step 304) as to whether the execution of the set of analyses is finished, either because the list of analytes of interest has been exhausted or because a time limit has been reached. If it is determined that the execution of analyses is finished, then the method 300 terminates or exits at step 305; otherwise, execution continues at step 306.

At the earliest times represented in the hypothetical graph of FIGS. 10A-10B, the quantity or abundance of ions of the particular diagnostic parent ion species that is generated by an ion source is below a predetermined threshold, represented by horizontal line 202. During this initial time period, the operating mode of the FAIMS apparatus is set to "non-dispersive" (wherein, by way of non-limiting example, compensation voltage and dispersion voltage are not applied or a symmetrical waveform is applied or a low-amplitude asymmetrical waveform is applied) such that the FAIMS apparatus acts as a passive transmission device for all ions and does not disperse ions according to their respective ion mobilities or differential ion mobilities. At the same time, a mass analyzer of the mass spectrometer repeatedly performs survey scans so as to monitor for the presence of at least one of the various diagnostic parent ion species of interest. At a certain time, indicated generally as elution-start time 204, the detected intensity of one of the diagnostic parent ion species will breach a predetermined threshold level, represented by horizontal line 202 in FIGS. 10A-10B. The above-outlined sequence of operations is represented by steps 306-312 of the method 300 depicted in FIG. 13. These steps are described in greater detail below.

In step 306 of the method 300 (FIG. 13), the FAIMS apparatus is set to its "non-dispersive" operating mode in which it acts as a device that passively and non-selectively transmits ions from an ion source to a mass spectrometer. In step 309, the exclusion list is checked so as to determine if any m/z ratios should be removed from the exclusion list and such m/z ratios are removed from the list. The decision to remove m/z ratio items from the exclusion list will generally be based on the amount of time that the items have been on the list, but may be based on other criteria. In the loop-comprising steps 310, 326 and 312, the detected abundances of the various m/z ratios of the analyte species (specifically, precursor species) of interest are queried, one-by-one, to determine if any is above a threshold level. This is accomplished by causing the mass analyzer to cycle through attempted detection, in step 310, of m/z ratios on the analyte precursor list, in sequence. The intervening decision step 326 between steps 310-312 ensures that execution of the method ends (at step 327) if the analyte species are exhausted during this query process. Once an abundance above threshold is identified in step 312, the method 300 branches to step 314.

It is assumed, for purposes of this example, that peak 200 corresponds to the detection of the ion species m1. Once abundance above the threshold value 202 is determined (at time, t=13.627 seconds, according to the example illustrated in FIGS. 10A-10B), the FAIMS apparatus configuration is changed from "non-dispersive" mode to "on m1" operating mode so that only the ion species m1 will be transmitted to the mass spectrometer and be detected during the remaining time period corresponding to peak 200. This operation corresponds to step 314 of the method 300 depicted in FIG. 13. Accordingly, as schematically illustrated in the bottom portions of FIGS. 10A-10B, the FAIMS-MS system may repeatedly measure the abundance of ion species m1, but does not detect any other ion species (m2, m3, etc) during this period. These other species are illustrated with patterning in FIG. 10A to indicate that detection of such species is inactive during the time period corresponding to peak 200. When configured in the "on m1" mode, the FAIMS apparatus transmits only those ions that have FAIMS ion mobility properties corresponding to those of the ion m1. In other words, the CV and DV of the FAIMS waveform are set, in this step, so as to transmit ions of the m1 ion species, if present, completely through the FAIMS while neutralizing ions that have differential ion mobility properties that are not similar to those of ion species m1.

Immediately after the step of setting the FAIMS apparatus so as to selectively transmit the ion species m1, as described above, the mass spectrometer may optionally delay operations for a delay period, LT, occurring over a delay time period, $w_f$, as shown in FIG. 10B. The delay time period, $w_f$, is primarily determined by the FAIMS residence time (plus shorter delay times associated with transit into the mass analyzer) and is assumed to be 100 ms in the illustrated example. During this delay period, which is implemented in the optional step 315 of the method 300 (FIG. 13), any ions species, including ion species m1 (if present), having the ion mobility properties corresponding to the selected DV and CV progress through the FAIMS apparatus from the ion inlet orifice to the ion outlet orifice without neutralization while other ions are neutralized in the FAIMS apparatus. At the end of the delay time period, $w_f$, the mass analyzer receives the first of the ions completely transmitted through the FAIMS apparatus after the onset of the FAIMS "on m1" mode. Note that the ions generated by an ion source and transmitted to the mass spectrometer through the FAIMS apparatus may be considered to be potential precursor ions for a subsequent ion fragmentation or ion reaction step (step 320).

The operation of the mass spectrometer may include further filtering of the ions received from the FAIMS apparatus according to m/z. For instance, in the example presently under discussion, the operation of a quadrupole mass filter (i.e., Q1) may be controlled so as to transmit substantially only ions having a mass-to-charge ratio of $(m/z)_1$, the mass-to-charge ratio of the expected ion species, m1. However, it should be noted that, although the expected ion species, m1, has a mass-to-charge ratio of $(m/z)_1$, other interfering ion species may fortuitously have this same mass-to-charge ratio. Thus, the detection of ion species having mass-to-charge ratio of $(m/z)_1$ and above threshold intensity (in step 312) may possibly be caused by such interfering species. Thus, while the FAIMS apparatus is operated in the "on m1" mode, the mass analyzer may be configured so as to perform—perhaps repeatedly—shortened or abridged ion surveys to determine if ion species having mass-to-charge ratio $(m/z)_1$ are still present in the ion stream received by the mass analyzer. This operation corresponds to step 316 of the method 300 depicted in FIG. 13. For example, if the mass analyzer comprises a mass filter, such as a quadrupole mass filter, then the mass filter can be operated so as to transmit, to a detector, only ions having mass-to-charge ratios substantially equal to $(m/z)_1$ while preventing the transmission of other ions.

If ions having mass-to-charge ratio $(m/z)_1$ fail to be detected immediately after configuring the FAIMS to operate in the "on m1" mode, then the determination in step 318 of method 300 evaluates to "N" (i.e., "no") and also, in step 322, it is subsequently determined that (because of interference) an insufficient quantity of data has been determined to define an ion chromatogram peak (the "N" branch of step 322 is executed). Under the assumption that the FAIMS apparatus has been configured properly and is operating properly, then it may be concluded, in such an instance, that the ions of this m/z ratio that were earlier detected at an above-threshold level (step 312) were not of the species m1 but, rather, of an interfering ion species having a fortuitously similar m/z ratio. Thus, in step 325, the mass-to-charge ratio of $(m/z)_1$ is added to the dynamic exclusion list such that a waiting period is set. Afterwards, provided that the list of analytes of interest has not been exhausted (step 326), then the method 300 returns to step 310 to search for another ion species having an abundance above threshold and an m/z ratio that is not on the exclusion list.

The ion exclusion list represents a list of ion species m/z ratios that will be temporarily excluded from selective transmission through the FAIMS to the mass spectrometer. In other words, during the time that $(m/z)_1$ is on the exclusion list (for example, an average, typical or expected peak width of a chromatographic peak, such as 12 seconds), the mass analyzer will, in steps 308-312, automatically ignore ion species of this mass-to-charge ratio and the species m1 will be excluded from FAIMS isolation (in step 314) because the isobaric interference species is considered to be present in the ion stream. During the time that the species m1 is excluded from FAIMS isolation and mass spectrometer detection, the mass spectrometer may, in steps 310-312 of the method 300, search for the presence of other ion species to be analyzed (e.g., species m2, m3, m4, . . . , m100 according to the example shown) that are not on the exclusion list or on the completion list (if utilized) and that are above their respective abundance thresholds in the most-recently obtained mass spectrum. If the mass to charge ratio of one of such species is detected above threshold, then the steps 314-318 may be repeated with regard to that species.

Returning to the discussion of step 318, if ions having mass-to-charge ratio $(m/z)_1$ continue to be detected above the threshold level 202 after the initial delay period, LT, then it may be concluded that the analyte species m1 (and not an isobarically interfering species) has indeed been detected and, in this case, the FAIMS apparatus remains configured in the "on m1" operating mode as the steps 316-321 are repeatedly executed. Steps 316 and 318 have already been discussed; step 320 comprises performing ion fragmentation or other ion-ion or ion-molecule reaction, using the ions selectively transmitted through the FAIMS apparatus as precursor ions, so as to generate product ions, in known fashion. The various product ions or a subset of the product ions are mass analyzed and detected (step 321) so as to generate a mass spectrum of each batch of product ions. The precursor ions may be further filtered, according to mass-to-charge ratio, by passing through a mass filter (for example, mass filter Q1) before being introduced to a collision cell or reaction cell. The incoming precursor ion species are repeatedly fragmented or otherwise reacted, in the collision or reaction cell, during the course of elution of the chemical compound that gives rise to the m1 ion species. During this time, the FAIMS apparatus serves as an ion filter that filters the incoming ions according to their FAIMS ion mobilities so as to eliminate isobarically interfering species and reduce overall background "noise" such that the m1 ion species may be reliably detected, even at low abundance levels.

The method 300 cycles through the steps 316-320 until the detected abundance drops below the threshold level 202 at elution-end time 205. In this case, the determination made in decision step 318 causes execution of the method 300 to branch to step 322. In this instance, the obtained MS/MS data are recorded in step 324. The analyte species for which the MS/MS data have been obtained may be added to a completion list in step 324. Alternatively, the ion species may be simply be deleted from a list of species to be analyzed. Execution of the method 300 then returns to step 304.

In some alternative embodiments (see FIG. 11 and FIG. 14), an initial survey chromatographic run may be performed, with the FAIMS in "non-dispersive" mode throughout the survey data acquisition, in which the elution times of various prospective or potential analyte precursor ions—such as those from a list of precursor analyte ions of interest—are measured and recorded. The recorded events will include a respective elution-start time and elution-end time for each of the prospective or potential analyte precursor ions. During the survey scan, precursor ions corresponding to analyte ions of interest may also be isolated and fragmented so as to generate multiple MS/MS spectra, in conventional fashion. Nonetheless, in many circumstances of low abundance analytes, the lower limit of quantitation of the analytes may be improved by repeating the multiple reaction monitoring analyses, after the survey experiment, using a FAIMS device to filter the incoming ions prior to their introduction into a mass spectrometer.

Figure 11:
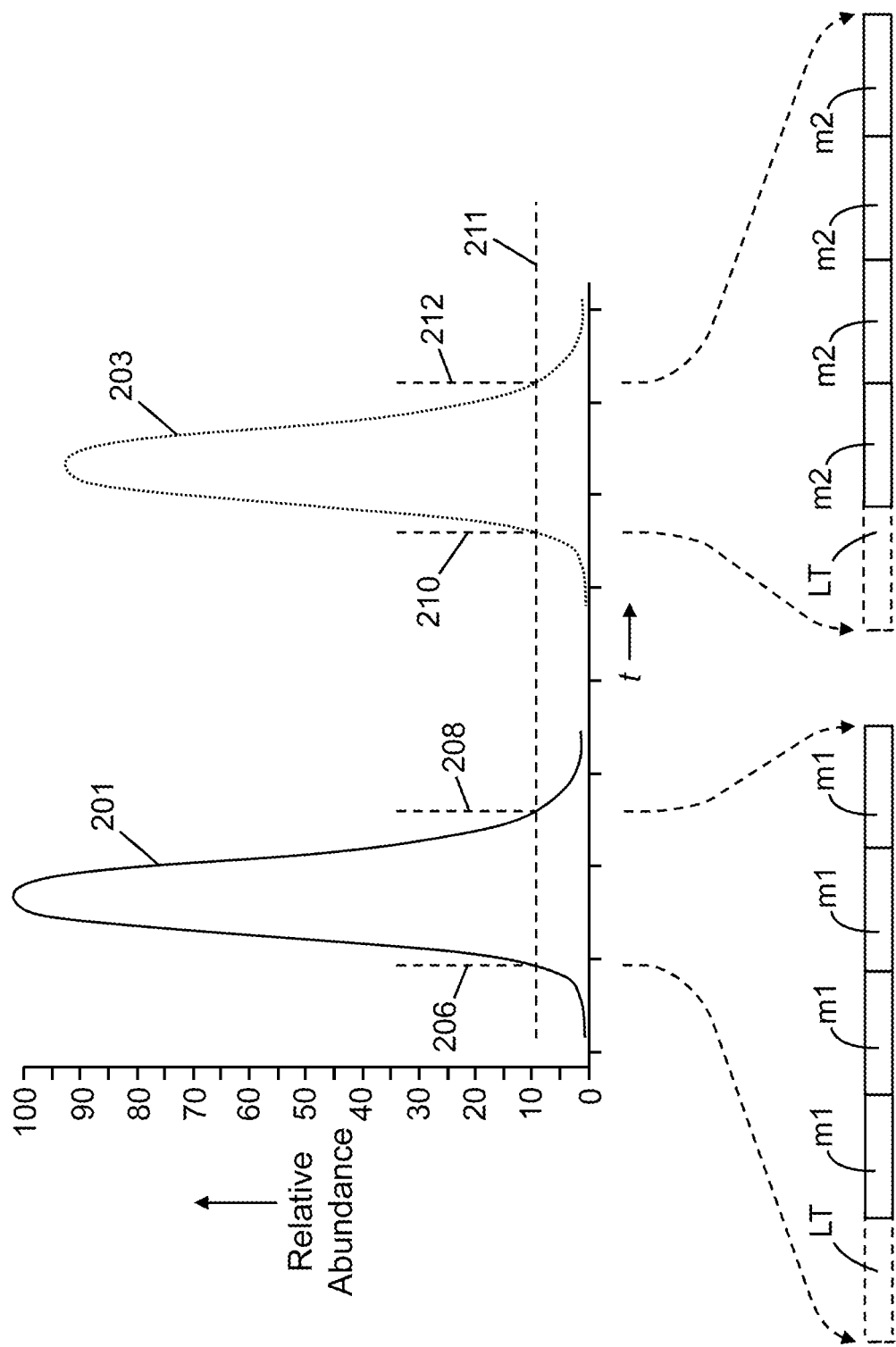
FIG. 11 is a schematic depiction of a sequence of events occurring, in accordance with some embodiments according to the present teachings, during multiple-reaction monitoring during the elution of multiple separated chromatographic peaks using a system comprising a FAIMS apparatus coupled to a mass spectrometer.

For example, FIG. 11 illustrates a hypothetical situation of two well-resolved chromatographic peaks, peaks 201 and 203, where each such peak corresponds to elution of a single respective analyte compound, corresponding to ion species m1 and ion species m2 as shown. An initial survey chromatographic experiment can be used to identify the elution start time 206 and the elution end time 208 of the first eluting analyte and the elution start time 210 and the elution end time 212 of the other analyte. During the survey experiment, the FAIMS apparatus is maintained in its "non-dispersive" condition. In the example shown in FIG. 11, the elution start and elution end times are defined by the points at which the peaks cross the signal threshold value 211; however, separate thresholds could be defined for each respective peak. Subsequent to the survey experiment, a second chromatographic experiment is performed using a second batch of the same sample, where the only difference between the survey experiment and the second chromatographic experiment is that, in the latter case, the FAIMS apparatus is set to its appropriate "on" condition at appropriate times.

Figure 14:
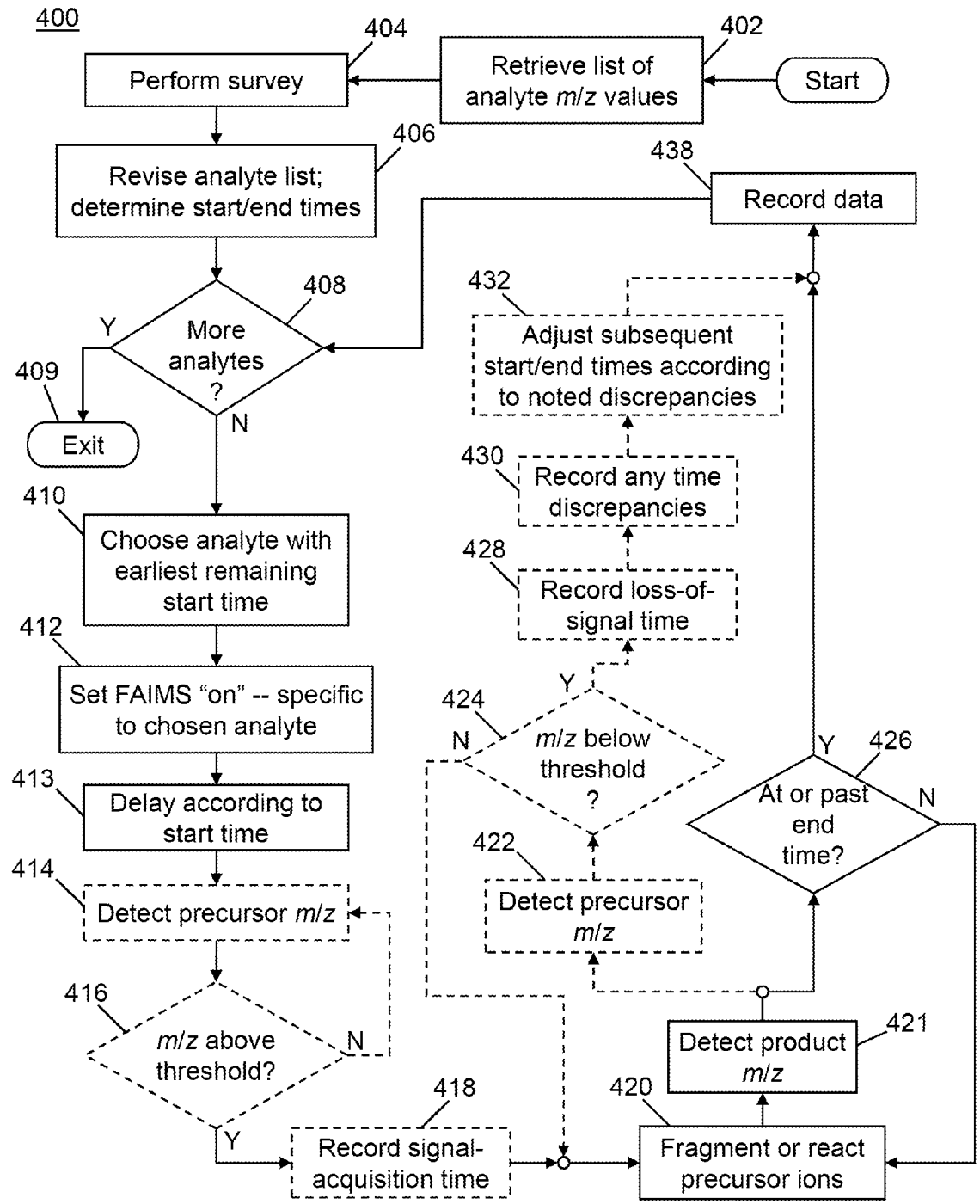
FIG. 14 is a flow diagram of a second method for operating an analytical system comprising a liquid chromatograph, a FAIMS apparatus and a mass spectrometer in accordance with the second teachings.

An exemplary method consistent with the graphical depiction of FIG. 11 is provided in flow diagram form in FIG. 14. In step 402 of the method 400 (FIG. 14), information pertaining to the various diagnostic analyte of species of interest may be retrieved or input, either from an electronic storage device are from user data entry. The retrieved information comprises at least a list of respective mass-to-charge (m/z) values, as expected to be generated by an ionization source, of the various analyte species of interest. The retrieved information may further comprise information pertaining to product ion species to be formed by reaction or fragmentation of each respective diagnostic ion species generated by the ion source and may further include mass spectrometer operational parameter settings required to detect or fragment the ions. The information may also include parameters pertaining to FAIMS settings to be employed in conjunction with the detection of each such ion species. Such FAIMS settings may include various compensation voltage (CV) and dispersion voltage (DV) settings to be used so as to cause the FAIMS apparatus to transmit each respective diagnostic ion species completely through the FAIMS apparatus to the mass spectrometer while simultaneously neutralizing and eliminating other ion species.

In the step 404 of the method 400 (FIG. 14), a preliminary survey chromatographic experimental run is performed as described above. The survey may determine that not all ion species of interest are present in the sample. Accordingly, in step 406, the list of analyte ion species to be searched for may be modified, based on information obtained from the prior survey. Since the survey data will include information relating to the detected abundance of various ions versus retention time, a list of elution start times and elution end times (such as the elution start times 206 and 210 and the elution end times 208 and 212 illustrated in FIG. 11) may be derived from the survey data and recorded in step 406. Further, each of the set of elution start times and the set of elution end times may be sorted according to increasing retention time in step 406. Strictly speaking, these derived elution start and elution end times do not exactly correspond to actual beginning and ending times of emission of compounds from a chromatographic column. Instead, the derived elution start time and elution end time discussed herein are determined from the points at which the measured ion abundances cross threshold values 211 (FIG. 11).

The subsequent steps 408-438 of the method 400 (FIG. 14) comprise an iterated loop of steps which relate to a subsequent LCMS-FAIMS-MS/MS experimental run, using a system having a FAIMS apparatus coupled to a mass spectrometer. The LCMS-FAIMS-MS/MS experimental run makes use of data obtained in the prior survey experiment, as previously described. During each iteration of steps 408-438, a determination is made (step 408) as to whether the execution of the set of analyses is finished, either because the list of analytes of interest (possibly as revised in step 406) has been exhausted or because a time limit has been reached. If it is determined that the execution of analyses is finished, then the method 400 terminates or exits at step 409; otherwise, execution continues at step 410.

The method 400 as shown in FIG. 14 includes optional steps and execution pathways—indicated by dashed lines—that may be executed in case the chromatography elution times are not sufficiently reproducible between the initial survey experiment and the subsequent experiment including FAIMS ion filtering. If the chromatography results are adequately reproducible, then the method 400 may follow the set of general steps and flow pathways indicated by solid lines—specifically, steps 408-413 followed by the possibly-iterated set of three steps 420, 421 and 426 followed by step 438. If the chromatography results are considered to be not adequately reproducible, then adjusted elution start and elution end times may be obtained during the course of the post-survey chromatography. In this latter situation, the steps 408-412 are executed and followed by the possibly-iterated set of two steps 414 and 416 after which these steps are followed by step 418 which is then followed by the possibly-iterated set of steps 420, 421, 422 and 424, which are then followed by steps 428-438.

For execution of the following steps of the method 400, it is preferable that each of the set of elution start times and the set of elution end times is sorted according to increasing retention time. In step 410, a selection is made, from the remaining analytes that have not yet been analyzed in the LCMS-FAIMS-MS/MS experimental run, of the analyte ion species corresponding to the earliest elution start time (i.e., the next eluting analyte ion species), as determined in step 406. In step 412, the FAIMS operational mode is set to "on" and is specific to the properties of the analyte ion species selected in step 410. For example, with reference to FIG. 11, if the selected analyte ion species is m1, corresponding to the peak 201, then the FAIMS operational mode would be set to "on m1" in step 412, using the terminology described previously in this document.

The step 413 of the method 400 (FIG. 14) is a waiting step in which execution of the method 400 is delayed until a time that is determined in accordance with the elution start time of the chosen analyte. In various embodiments, the delay may last until the experimental retention time advances so as to equal or exceed the elution start time of the next eluting analyte ion species, after which step 420 is executed. However, in various other embodiments in which the chromatographic elution start time may be considered to be insufficiently reproducible as described above, the delay may last a shorter period such that the mass spectrometer precursor ion detection step 414 is executed prior to the previously determined elution start time of the chosen analyte, thereby allowing earlier-than-expected elution to be detected. In this situation, steps 414 and 416 are repeated until the detected intensity of ions having the m/z ratio of the chosen analyte breaches a threshold level. The time at which the threshold is exceeded (here termed "signal-acquisition time") is then recorded in step 418.

After either the actual experimental time has met or exceeded the previously determined elution start time or the detected intensity of the chosen m/z ratio has breached the threshold, a set of mass spectrometer operation steps including ion fragmentation (or other ion reaction) in step 420 and ion detection in step 421 are iterated until a stopping condition is reached. If the reproducibility of the chromatography is trusted, then steps 420, 421 and 426 are repeatedly executed until the actual experimental time equals or exceeds the expected elution end time of the analyte ion species under consideration. Otherwise, if the reproducibility of the chromatography results is considered to be insufficiently adequate to permit the previously-determined elution end time to be used as the stopping condition, then steps 420-424 are repeated until the detected intensity of precursor ions drops below a threshold.

During execution of either the set of steps 420, 421 and 426 or the set of steps 420-424, the FAIMS apparatus retains its setting, as set in step 412, so as to transmit the selected precursor ion species (ion species m1, for example) and to neutralize all or most other ion species. During these same steps, a mass filter stage of the mass spectrometer (for example, Q1) may be set so as to transmit, to a fragmentation or other ion reaction cell, a batch of ions comprising only ion species having a mass-to-charge (m/z) ratio value that is substantially equal to the m/z value of the selected ion species. The selected ion species thus comprises a precursor ion species that is fragmented or otherwise reacted in the fragmentation or reaction cell in step 421 so as to generate product ions, in known fashion. If the execution pathway of the method 400 proceeds as shown by the dashed lines, then the step 421 of detecting product ions is followed by the step 422 of detecting analyte precursor ions so as to detect, in real time, if the elution of the selected analyte has attained its effective end time such that the detected intensity of the analyte precursor ions has dropped below a threshold value (as determined in step 424).

If the execution pathway of the method 400 proceeds as shown by the dashed lines, then, after the detected intensity of analyte precursor ions has dropped below a threshold value, as determined in step 424, then the time at which the detected intensity has fallen below the threshold is noted in step 428 as "loss-of-signal time" with respect to the particular analyte. The "signal-acquisition time" and "loss-of-signal time" are then compared, in step 430, to the expected elution start time end elution end time, respectively, pertaining to the chosen analyte, where these expected times are as determined in the prior survey experiment. Any discrepancies noted between the signal-acquisition time and the expected elution start time or between the loss-of-signal time and the expected elution end time may then be used, in step 432, to adjust the expected elution start and elution end times of subsequently eluting analytes. In many experiments, the various elution start and elution end times may all shift by an essentially constant time increment between the survey experiment and the subsequent experiment employing FAIMS ion filtering. In such situations, the set of steps and execution pathways indicated by dashed lines in FIG. may only be need to executed one time—with regard to the first eluting analyte—or, possibly a few times with regard to the first few eluting analytes.

Figure 12:
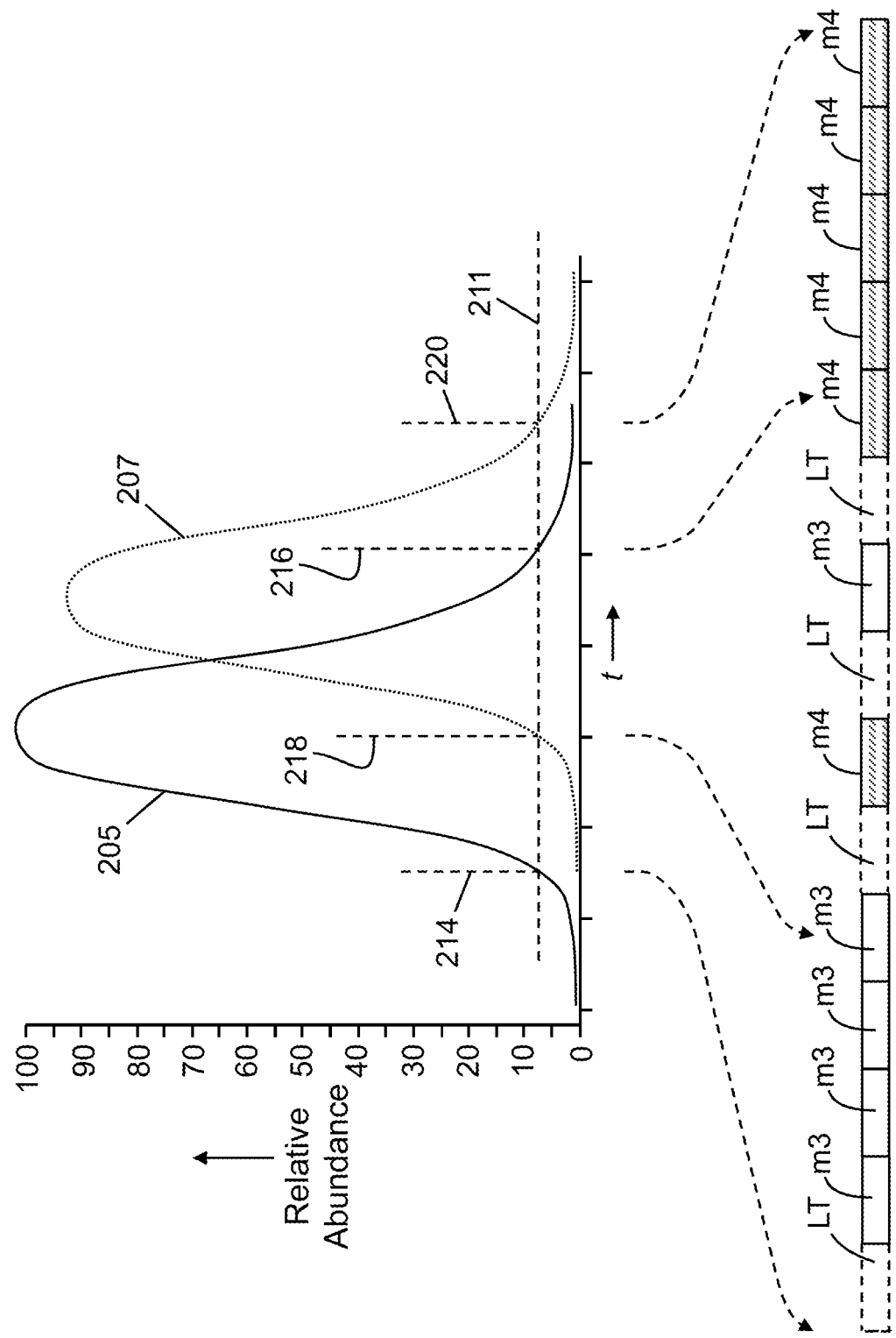
FIG. 12 is a schematic depiction of a sequence of events occurring, in accordance with some embodiments according to the present teachings, during multiple-reaction monitoring during the elution of multiple partially overlapping chromatographic peaks using a system comprising a FAIMS apparatus coupled to a mass spectrometer.

FIG. 12 illustrates a situation that is similar to that shown in FIG. 11 except that the analyte compounds that give rise to ion species m3 and to ion species m4 partially co-elute. A preliminary survey chromatographic experiment can determine that the elution start time and end time, as determined by threshold crossings, of peak 205 occur at time 214 and 216, respectively. Likewise, the survey experiment can determine that the elution start time and end time of peak 207 occur at time 218 and 220, respectively. Between elution start time 218 of peak 207 and elution end time 216 of peak 205, the abundance of both ion species m3 and m4 is above threshold. In this situation, the exemplary method illustrated in FIG. 14 may be modified, in relatively straightforward fashion, so as to account for the detection of co-eluting analytes. The modified method of analysis may include a list of co-eluting analytes which is initially empty but to which a list item is added every time an expected elution start time is reached and from which a list item is deleted every time that an elution end time is reached. The modified method will then include steps of cycling through the list of co-eluting analytes one at a time. As each one of the co-eluting analytes is considered in turn, the FAIMS apparatus may be configured so as to transmit precursor ions generated from that analyte to the mass spectrometer. At the same time, an associated control system (not shown) may be configured to operate the mass spectrometer so as fragment or otherwise react the precursor ions so as to generate product ions (possibly after isolation of the precursor ions) and to store data relating to the product ions generated from the precursor ions corresponding to the particular analyte. After each such detection event, the system time (e.g., experimental run time) may be noted and used to determine if a previously listed analyte should be removed from or an additional analyte should be added to the end of the list of co-eluting analytes. Subsequently, the FAIMS apparatus may be re-configured so as to transmit the next analyte on the list to the mass spectrometer and the process repeats.

The discussion included in this application is intended to serve as a basic description. Although the present invention has been described in accordance with the various embodiments shown and described, one of ordinary skill in the art will readily recognize that there could be variations to the embodiments or combinations of features in the various illustrated embodiments and those variations or combinations of features would be within the spirit and scope of the present invention. The reader should thus be aware that the specific discussion may not explicitly describe all embodiments possible; many alternatives are implicit. As but one example, FIGS. 5A-5B illustrate a FAIMS apparatus comprising both an ion inlet orifice 152 that has curved walls and that protrudes into a gas expansion chamber and also comprising multiple gas inlet conduits 113 providing FAIMS bath gas to the expansion chamber from opposing sides. Although both such features are beneficial, the benefits of the novel ion inlet orifice configuration could also be realized using a conventional single gas inlet conduit. As another example, although the FAIMS bath gas is illustrated as being provided through "conduits", any form of gas inlet could suffice, such as for example, gas inlet "apertures". Similarly, although the ion inlet is described herein as an "orifice", it could equally take the form of or be described as an "aperture" or, in some embodiments, a "conduit".

It should further be realized that, although the methods of instrumental operation described herein (e.g., method 300 and method 400) have been described with specific reference to FAIMS apparatuses, such apparatuses are only one example of the general class of apparatuses known as ion mobility apparatuses. The various ion mobility apparatuses may be employed as ion mobility spectrometers and various types may be employed as a controllable or adjustable pre-filter that is coupled between an ion source and a mass spectrometer. It is believed that the FAIMS apparatus embodiments disclosed herein provide particular advantages when employed to filter ions and to transmit ions to a mass spectrometer. However, it should be readily appreciated that, although the methods described herein refer to the use of a FAIMS-type of ion mobility apparatus, other types of ion known ion mobility devices could be substituted for a FAIMS device, without departing from the novel aspects of these methods. Operation of a non-FAIMS ion mobility apparatus in a "non-dispersive" mode (analogous to FAIMS OFF mode previously described herein) could include discontinuing application of an electrical potential difference to electrodes that, during normal operation, urge ions through a drift tube and, possibly, initiating a flow of carrier gas through the drift tube so as to cause a flow of the ions through the drift tube.

It should be further appreciated that, although various aspects of the above description refer to the use of liquid chromatography in conjunction with ion spectrometry, other type of chromatograph apparatuses—such as a gas chromatograph apparatuses—are frequently used to supply analyte molecules to either mass spectrometers, FAIMS apparatuses, or to other types of ion mobility apparatuses. Thus, the system and method embodiments described herein may be coupled to gas chromatographs or other types of chromatograph apparatuses or employed with such apparatuses without departing from the novel aspects of the invention. Any references to liquid chromatographs or to liquid chromatography could be substituted by references to another form of chromatograph or chromatography without departing from these novel aspects.

Accordingly, many modifications may be made by one of ordinary skill in the art without departing from the scope and essence of the invention. Neither the description nor the terminology is intended to limit the scope of the invention—the invention is defined only by the claims. Any patents, patent applications or other publications mentioned herein are hereby explicitly incorporated herein by reference. Any such patents, patent applications or other publications are incorporated in in their respective entirety except that, in case of any contradiction between the incorporated item and the present specification, the present specification shall be controlling.

What is claimed is:

1. A method of operating a system comprising a chromatograph operable to separate sample solutions into fractions, an ion source operable to ionize components of the fractions and a mass spectrometer operable to analyze and detect the ions, the method comprising:
   (a) providing an abundance threshold value and a list comprising respective entries for each of two or more precursor ion species of interest comprising respective precursor-ion m/z ratios;
   (b) transmitting a first portion of a sample fraction comprising a plurality of sample-fraction ion species through an ion mobility spectrometer to the mass spectrometer, wherein the ion mobility spectrometer is operated in a non-dispersive mode;
   (c) detecting a respective ion abundance at each of a plurality of sample-fraction m/z ratios using the mass spectrometer; and
   (d) upon detection of an above-threshold ion abundance at a sample-fraction m/z-ratio corresponding to a first one of the precursor ion species of interest:
      (d1) inletting a second portion of the sample fraction into the ion mobility spectrometer, wherein the ion mobility spectrometer is operated in dispersive mode such that ions of the first precursor-ion species are preferentially transmitted through the ion mobility spectrometer to the mass spectrometer;
      (d2) fragmenting the preferentially-transmitted ions so as to generate a first set of product ion species; and
      (d3) detecting the first set of product ion species using the mass spectrometer.

2. A method as recited in claim 1, wherein the step (b) of transmitting the first portion of the sample fraction through an ion mobility spectrometer comprises transmitting said first portion of the sample fraction through a high field asymmetric waveform ion mobility spectrometry (FAIMS) spectrometer.

3. A method as recited in claim 2, wherein the operating of the FAIMS spectrometer in dispersive mode comprises transmitting the first precursor-ion species within a gas having a gas flow rate through an annular separation region of the FAIMS spectrometer from an ion inlet port to an ion exit port, wherein the gas flow rate and a flow path length between the ion inlet and ion exit ports are such that a residence time of the first precursor-ion species within the FAIMS spectrometer is less than or equal to 10 milliseconds.

4. A method as recited in claim 2, wherein the step (d1) of inletting the second portion of the sample fraction into the ion mobility spectrometer operated in dispersive mode comprises operating the FAIMS spectrometer under application of an asymmetric oscillatory dispersion voltage (DV) and a non-oscillatory compensation voltage (CV) across electrodes of the FAIMS spectrometer, wherein said applied DV and CV are chosen so as to preferentially transmit ions of the first precursor ion species through the FAIMS spectrometer.

5. A method as recited in claim 4, wherein the step (b) of transmitting the first portion of the sample fraction through the ion mobility spectrometer operated in the non-dispersive mode comprises transmitting the first portion of the sample fraction through the FAIMS spectrometer in the absence of application of both the CV and the DV to the electrodes.

6. A method as recited in claim 4, wherein the step (b) of transmitting the first portion of the sample fraction through the ion mobility spectrometer operated in the non-dispersive mode comprises transmitting the first portion of the sample fraction through the FAIMS spectrometer during the application of a symmetric oscillatory waveform to the electrodes.

7. A method as recited in claim 4, wherein the providing of the list comprising respective entries for each of the two or more precursor ion species of interest comprises providing entries of the list wherein each entry includes FAIMS parameters necessary for causing the FAIMS spectrometer to preferentially transmit the respective precursor ion species therethrough.

8. A method as recited in claim 7, wherein the providing of the list comprising respective entries for each of the two or more precursor ion species of interest further comprises providing the entries wherein each entry includes the ink ratio of the respective precursor ion species of interest.

9. A method as recited in claim 1, wherein the step (d1) further includes detection of an abundance of ions, by the mass spectrometer, at the m/z ratio corresponding to the first precursor ion species of interest and wherein subsequent performing of the steps (d2) and (d3) is conditional upon said detected abundance at said corresponding m/z ratio being above the threshold.

10. A method as recited in claim 9, further comprising, if the detected abundance at said corresponding ink ratio is not above the threshold, adding said corresponding m/z ratio to a list of m/z ratios to be temporarily excluded from fragmentation.

11. A method as recited in claim 1, wherein the performing of the steps (d1) through (d3) is conditional upon the ink ratio corresponding to the first precursor ion species of interest being absent from a list of ink ratios that are to be temporarily excluded from fragmentation.

12. A method as recited in claim 1, further comprising:
   (e) transmitting a first portion of a second sample fraction through the ion mobility spectrometer to the mass spectrometer, wherein the ion mobility spectrometer is operated in the non-dispersive mode;
   (f) detecting a respective ion abundance at each of a plurality of second-sample-fraction ink ratios using the mass spectrometer; and
   (g) upon detection of an above-threshold ion abundance at a second-sample-fraction m/z-ratio corresponding to a second one the precursor ion species of interest:
      (g1) inletting a second portion of the second sample fraction into the ion mobility spectrometer, wherein the ion mobility spectrometer is operated in dispersive mode such that such that ions of the second precursor-ion species are preferentially transmitted through the ion mobility spectrometer to the mass spectrometer;
      (g2) fragmenting the preferentially-transmitted ions so as to generate a second set of product ion species; and
      (g3) detecting the second set of product ion species using the mass spectrometer.

13. A method as recited in claim 12, wherein the step (b) of transmitting the first portion of the sample fraction and the step (e) of transmitting the first portion of the second sample fraction through the ion mobility spectrometer comprises transmitting said first portions through a high field asymmetric waveform ion mobility spectrometry (FAIMS) spectrometer.

14. A method as recited in claim 13, wherein:
the step (d1) of inletting the second portion of the sample fraction into the ion mobility spectrometer operated in dispersive mode comprises operating the FAIMS spectrometer under application of a first asymmetric oscillatory dispersion voltage (DV) and a first non-oscillatory compensation voltage (CV) across electrodes of the FAIMS spectrometer, wherein said applied first DV and first CV are chosen so as to preferentially transmit ions of the first precursor-ion species through the FAIMS spectrometer; and
the step (g1) of inletting the second portion of the second sample fraction into the ion mobility spectrometer operated in dispersive mode comprises operating the FAIMS spectrometer under application of a second DV and a second CV across the electrodes of the FAIMS spectrometer, wherein said applied second DV and second DV are chosen so as to preferentially transmit ions of the second precursor ion species through the FAIMS spectrometer.

* * * * *

UNITED STATES PATENT AND TRADEMARK OFFICE
CERTIFICATE OF CORRECTION

PATENT NO. : 9,500,624 B2  
APPLICATION NO. : 14/738089  
DATED : November 22, 2016  
INVENTOR(S) : Satendra Prasad et al.

Page 1 of 1

It is certified that error appears in the above-identified patent and that said Letters Patent is hereby corrected as shown below:

In the Claims

Claim 8, Column 28, Line 21:  
Replace "wherein each entry includes the ink"  
With --wherein each entry includes the m/z--

Claim 10, Column 28, Line 31:  
Replace "said corresponding ink ratio"  
With --said corresponding m/z ratio--

Claim 11, Column 28, Line 37:  
Replace "is conditional upon the ink"  
With --is conditional upon the m/z--

Claim 11, Column 28, Line 39:  
Replace "from a list of ink ratios"  
With --from a list of m/z ratios--

Claim 12, Column 28, Line 47:  
Replace "second-sample-fraction ink ratios"  
With --second-sample-fraction m/z ratios--

Claim 12, Column 28, Line 55:  
Replace "such that such that ions"  
With --such that ions--

Claim 14, Column 29, Line 20/21:  
Replace "wherein said applied second DV and second DV are chosen"  
With --wherein said applied second DV and second CV are chosen--

Signed and Sealed this  
Twenty-fifth Day of April, 2017

Michelle K. Lee  
*Director of the United States Patent and Trademark Office*